US008691211B2

(12) United States Patent
Josephson

(10) Patent No.: US 8,691,211 B2
(45) Date of Patent: Apr. 8, 2014

(54) SUPPRESSION OF IMMUNE RESPONSE TO FACTOR VIII IN HEMOPHILIA A PATIENTS

(75) Inventor: Neil Cary Josephson, Seattle, WA (US)

(73) Assignee: Puget Sound Blood Center, Seattle, WA (US)

( * ) Notice: Subject to any disclaimer, the term of this patent is extended or adjusted under 35 U.S.C. 154(b) by 501 days.

(21) Appl. No.: 12/721,361

(22) Filed: Mar. 10, 2010

(65) Prior Publication Data

US 2010/0233119 A1    Sep. 16, 2010

Related U.S. Application Data

(60) Provisional application No. 61/159,021, filed on Mar. 10, 2009.

(51) Int. Cl.
*A61K 48/00* (2006.01)
*A61K 38/37* (2006.01)
*C12N 5/10* (2006.01)
*C12N 15/85* (2006.01)

(52) U.S. Cl.
USPC ..... 424/93.21; 514/14.1; 435/325; 435/320.1

(58) Field of Classification Search
USPC ............. 424/93.21; 514/14.1; 435/325, 320.1
See application file for complete search history.

(56) References Cited

U.S. PATENT DOCUMENTS 4,868,112 A    9/1989  Toole, Jr.
2005/0032215 A1  2/2005  Treco et al.

OTHER PUBLICATIONS

Su et al. (2006) Blood, vol. 108, Abstract 768.*
Reipert et al. (2001) Thromb. Haemost., vol. 86(6), 1345-1352.*
Griesenbach et al. (2001) Mol. Ther., vol. 5(2), 98-103.*
Peng et al. (2007) J. Autoimmun., vol. 29, 303-309.*
Lusher et al. (2004) J. Thromb. Haemostasis, vol. 2, 574-583.*
Meslier et al. (2011) J. Thromb. Haemos., vol. 9, 719-728.*
Ranges et al. (1987) Cellular Immunology, vol. 106, 163-173.*
Chace et al. (1994) J. Immunol., vol. 152, 405-412.*
Propper et al. (1992) Transplantation, vol. 54(6), 1058-1063.*
Andersson, L-O. et al., "Isolation and Characterization of Human Factor VIII: Molecular Forms in Commercial Factor VIII Concentrate, Cryoprecipitate, and Plasma," Proc. Natl. Acad. Sci. USA, May 1986, pp. 2979-2983, vol. 83.
Bennett, S.R.M. et al., "Help for Cytotoxic-T-Cell Responses is Mediated by CD40 Signalling," Nature, Jun. 4, 1998, pp. 478-480, vol. 393.
Bi, L. et al., "Targeted Disruption of the Mouse Factor VIII Gene Produces a Model of Haemophilia A," Nature Genetics, May 1995, pp. 119-121, vol. 10.

Bi, L. et al., "Further Characterization of Factor VIII-Deficient Mice Created by Gene Targeting: RNA and Protein Studies," Blood, 1996, pp. 3446-3450, vol. 88.
Chen, W. et al., "TGF-β Released by Apoptotic T Cells Contributes to an Immunosuppressive Milieu," Immunity, Jun. 2001, pp. 715-725, vol. 14.
Colowick, A.B. et al., "Immune Tolerance Induction in Hemophilia Patients with Inhibitors: Costly Can Be Cheaper," Blood, 2000, pp. 1698-1702, vol. 96.
Dimichele, D., "Immune Tolerance Therapy for Factor VIII Inhibitors: Moving from Empiricism to an Evidence-Based Approach," Journal of Thrombosis and Haemostasis, 2007, pp. 143-150, vol. 5, Suppl 1.
Doering, C.B. et al., "High Level Expression of Recombinant Porcine Coagulation Factor VIII," The Journal of Biological Chemistry, Oct. 11, 2002, pp. 38345-38349, vol. 277, No. 41.
Evans, G.I. et al., "Genetic Induction of Immune Tolerance to Human Clotting Factor VIII in a Mouse Model for Hemophilia A," Proc. Natl. Acad. Sci. USA, May 1998, pp. 5734-5739, vol. 95.
Ferguson, T.A. et al., "Uptake of Apoptotic Antigen-Coupled Cells by Lymphoid Dendritic Cells and Cross-Priming of CD8 T Cells Produce Active Immune Unresponsiveness," The Journal of Immunology, 2002, pp. 5589-5595, vol. 168.
Fulcher, C.A. et al., "Localization of Human Factor FVIII Inhibitor Epitopes to Two Polypeptide Fragments," Proc. Natl. Acad. Sci USA, Nov. 1985, pp. 7728-7732, vol. 82.
Hay, C.R.M. et al., "The Diagnosis and Management of Factor VIII and IX Inhibitors: a Guideline from the United Kingdom Haemophilia Centre Doctors Organisation," British Journal of Haematology, 2006, pp. 591-605, vol. 133.
Iyoda, T. et al., "The CD8+ Dendritic Cell Subset Selectively Endocytoses Dying Cells in Culture and In Vivo," J. Exp. Med., May 20, 2002, pp. 1289-1302, vol. 195, No. 10.
Josephson, N.C. et al., "Transduction of Long-Term and Mobilized Peripheral Blood-Derived NOD/SCID Repopulating Cells by Foamy Virus Vectors," Human Gene Therapy, Jan. 2004, pp. 87-92, vol. 15.
Kim, S. et al., "Transcriptional Suppression of Interleukin-12 Gene Expression Following Phagocytosis of Apoptotic Cells," Immunity, Nov. 2004, pp. 643-653, vol. 21.
Lander, M.R. et al., "A Procedure for Culture of Cells from Mouse Tail Biopsies: Brief Communication," J Natl Cancer Inst, Feb. 1978, pp. 477-478, vol. 60, No. 2.
Lannutti, B.J. et al., "Identification and Activiation of Src Family Kinases in Primary Megakaryocytes," Experimental Hematology, 2003, pp. 1268-1274, vol. 31.
Liu, K. et al., "Immune Tolerance After Delivery of Dying Cells to Dendritic Cells in Situ," J. Exp. Med., Oct. 21, 2002, pp. 1091-1097, vol. 196, No. 8.

(Continued)

*Primary Examiner* — Anne Marie S Wehbe
(74) *Attorney, Agent, or Firm* — Fenwick & West LLP

(57) ABSTRACT

This invention relates to methods and compositions for suppressing an immune response to Factor VIII in subjects suffering from hemophilia A and having preformed inhibitor antibodies against Factor VIII, and compositions and methods that advantageously render subjects amenable to standard treatments for hemophilia A, including Factor VIII replacement therapy.

26 Claims, 12 Drawing Sheets

(56) References Cited

OTHER PUBLICATIONS

Lusher, J. et al., "Human Recombinant DNA-Derived Antihemophilic Factor in the Treatment of Previously Untreated Patients with Hemophilia A: Final Report on a Hallmark Clinical Investigation," Journal of Thrombosis and Haemostasis, 2004, pp. 574-583, vol. 2.

Maeda, A. et al., "Intravenous Infusion of Syngeneic Apoptotic Cells by Photopheresis Induces Antigen-Specific Regulatory T Cells," The Journal of Immunology, 2005, pp. 5968-5976, vol. 174.

Mariani, G. et al., "Immune Tolerance in Hemophilia—Principal Results from the International Registry," Thrombosis and Haemostasis, 1994, pp. 155-158, vol. 72, No. 1.

Misra, N. et al., "Cutting Edge: Human $CD4^+ CD25^+$ T Cells Restrain the Maturation and Antigen-Presenting Function of Dendritic Cells," The Journal of Immunology, 2004, pp. 4676-4680, vol. 172.

Morelli, A.E. et al., "Internalization of Circulating Apoptotic Cells by Splenic Marginal Zone Dendritic Cells; Dependence on Complement Receptors and Effect on Cytokine Production," Blood, Jan. 15, 2003, pp. 611-620, vol. 101, No. 2.

Morfini, M. et al., "European Study on Orthopaedic Status of Haemophilia Patients with Inhibitors," Haemophilia, 2007, pp. 606-612, vol. 13.

Morita, Y. et al., "Dendritic Cells Genetically Engineered to Express IL-4 Inhibit Murine Collagen-Induced Arthritis," The Journal of Clinical Investigation, May 2001, pp. 1275-1284, vol. 107, No. 10.

Moser, M., "Dendritic Cells in Immunity and Tolerance—Do They Display Opposite Functions?" Immunity, Jul. 2003, pp. 5-8, vol. 19.

Paisley, S. et al., "The Management of Inhibitors in Haemophilia A: Introduction and Systematic Review of Current Practice," Haemophilia, 2003, pp. 405-417, vol. 9.

Peng, Y. et al., "Innate and Adaptive Immune Response to Apoptotic Cells," Journal of Autoimmunity, Dec. 2007, pp. 303-309, vol. 29, No. 4.

Pittman, D.D. et al., Proteolytic Requirements for Thrombin Activation of Anti-Hemophilic Factor (Factor VIII), Proc. Natl. Acad. Sci. USA, Apr. 1988, pp. 2429-2433, vol. 85.

Probst, H.C. et al., "Inducible Transgenic Mice Reveal Resting Dendritic Cells as Potent Inducers of $CD8^+$ T Cell Tolerance," Immunity, May 2003, pp. 713-720, vol. 18.

Reipert, B.M. et al., "Characterization of Antibodies Induced by Human Factor VIII in a Murine Knockout Model of Hemophilia A," Thromb Haemost, 2000, pp. 826-832, vol. 84.

Rutella, S. et al., "Regulatory T Cells and Tolerogenic Dendritic Cells: from Basic Biology to Clinical Applications," Immunology Letters, 2004, pp. 11-26, vol. 94.

Sauter, B. et al., "Consequences of Cell Death: Exposure to Necrotic Tumor Cells, but Not Primary Tissue Cells or Apoptotic Cells, Induces the Maturation of Immunostimulatory Dendritic Cells," J. Exp. Med., Feb. 7, 2000, pp. 423-434, vol. 191, No. 3.

Scandella, D. et al., "Epitope Mapping of Human Factor VIII Inhibitor Antibodies by Deletion Analysis of Factor VIII Fragments Expressed in *Escherichia coli*," Proc. Natl. Acad. Sci. USA, Aug. 1988, pp. 6152-6156, vol. 85.

Scharrer, I. et al., "Incidence of Inhibitors in Haemophilia A Patients—A Review of Recent Studies of Recombinant and Plasma-Derived Factor VIII Concentrates," Haemophilia, 1999, pp. 145-154, vol. 5.

Sen, P. et al., "Apoptotic Cells Induce Mer Tyrosine Kinase-Dependent Blockade of $NF-_k B$ Activation in Dendritic Cells," Blood, Sep. 28, 2006, pp. 653-660, vol. 109.

Steinman, R.M. et al., "Tolerogenic Dendritic Cells," Annu. Rev. Immunol., 2003, pp. 685-711, vol. 21.

Stuart, L.M. et al., "Inhibitory Effects of Apoptotic Cell Ingestion Upon Endotoxin-Driven Myeloid Dendritic Cell Maturation," J. Immunol., 2002, pp. 1627-1635, vol. 168.

Su, R-J. et al., "Reduction of Anti-FVIII Inhibitor Titers in Hemophilic Mice Infused with Syngeneic Apoptotic Cells Expressing a Human FVIII Transgene," Blood (ASH Annual Meeting Abstracts), 2005, p. 216, Abstract 106.

Su, R-J. et al., "Induction of Tolerance to FVIII in Hemophilic Mice by Delivery of Apoptotic Syngeneic Fibroblasts Expressing a FVIII Transgene," Blood (ASH Annual Meeting Abstracts), 2006, p. 108, Abstract 768.

Su, R.J. et al. "Suppression of FVIII Inhibitor Formation in Hemophilic Mice by Delivery of Transgene Modified Apoptotic Fibroblasts," Molecular Therapy, 2010, pp. 214-222, vol. 18, No. 1.

Thompson, A.R. et al., "Removal of Heparin and Protamine from Plasma," J. Lab. Clin. Med., Dec. 1976, pp. 922-929, vol. 88, No. 6.

Toole, J.J. et al., "A Large Region (≈95 kDa) of Human Factor VIII is Dispensible for in Vitro Procoagulant Activity," Proc. Natl. Acad. Sci. USA, Aug. 1986, pp. 5939-5942, vol. 83.

Trobridge, G. et al., "Improved Foamy Virus Vectors with Minimal Viral Sequences," Molecular Therapy, Sep. 2002, pp. 321-328, vol. 6, No. 3.

Vigoroux, S. et al., "Antigen-Induced Regulatory T Cells," Blood, Jul. 1, 2004, pp. 26-33, vol. 104, No. 1.

Voll, R.E. et al., "Immunosuppressive Effects of Apoptotic Cells," Nature, Nov. 27, 1997, pp. 350-351, vol. 390.

Wang, Z. et al., "Use of the Inhibitory Effect of Apoptotic Cells on Dendritic Cells for Graft Survival Via T-Cell Deletion and Regulatory T Cells," American Journal of Transplantation, 2006, pp. 1297-1311, vol. 6.

Wu, H. et al., "Mechanism of the Immune Response to Human Factor VIII in Murine Hemophilia A," Thromb Haemost, 2001, pp. 125-133, vol. 85.

Wyllie, A.H., "Apoptosis and Carcinogenesis," European Journal of Cell Biology, Jul. 1997, pp. 189-197, vol. 73.

Yang, L. et al., "Engineered Lentivector Targeting of Dendritic Cells for In Vivo Immunization," Nature Biotechnology, Mar. 2008, pp. 326-334, vol. 26, No. 3.

Ye, P. et al., "Naked DNA Transfer of Factor VIII Induced Transgene-Specific, Species-Independent Immune Response in Hemophilia A Mice," Molecular Therapy, Jul. 2004, pp. 117-126, vol. 10, No. 1.

Zhang, Z-X. et al., "Identification of a Previously Unknown Antigen-Specific Regulatory T Cell and Its Mechanism of Suppression," Nature Medicine, Jul. 2000, pp. 782-789, vol. 6, No. 7.

Gouw, S.C. et al., "F8 Gene Mutation Type and Inhibitor Development in Patients with Severe Hemophilia A: Systematic Review and Meta-Analysis," Blood, 2012, pp. 2922-2934, vol. 119.

Hay, C.R. et al., "The Principal Results of the International Immune Tolerance Study: a Randomized Dose Comparison," Blood, 2012, pp. 1335-1344, vol. 119.

Jellison, E.R. et al., "Distinct Mechanisms Mediate Naive and Memory CD8 T-Cell Tolerance," Proc. Natl. Acad. Sci. USA, Dec. 26, 2012, pp. 21438-21443, vol. 109, No. 52.

Kleinclauss, F. et al., "Intravenous Apoptotic Spleen Cell Infusion Induces a TGF-β-Dependent Regulatory T-Cell Expansion," Cell Death and Differentiation, 2006, pp. 41-52, vol. 13.

Madoiwa, S. et al., "Induction of Factor VIII-Specific Unresponsiveness by Intrathymic Factor VIII Injection in Murine Hemophilia A," J. Thromb. Haemost., 2009, pp. 811-824, vol. 7.

Madoiwa, S. et al., "Induction of Immune Tolerance by Neonatal Intravenous Injection of Human Factor VIII in Murine Hemophilia A," J. Thromb. Haemost., 2004, pp. 754-762, vol. 2.

Madoiwa, S. et al., "Immune Response Against Serial Infusion of Factor VIII Antigen Through an Implantable Venous-Access Device System in Haemophilia A Mice," Haemophilia, 2012, pp. e323-e330, vol. 18.

Mathis, D. et al., "Back to Central Tolerance," Immunity, May 2004, pp. 509-516, vol. 20.

Matzinger, P. "Tolerance, Danger, and the Extended Family," Annu. Rev. Immunol., 1994, pp. 991-1045, vol. 12.

Meslier, Y. et al., "Bortezomib Delays the Onset of Factor VIII Inhibitors in Perimental Hemophilia A, But Fails to Eliminate Established Anti-Factor VIII IgG-Producing Cells," J. Thromb. Haemos., 2011, pp. 719-728, vol. 9.

Moghimi, B. et al., "Induction of Tolerance to Factor VIII by Transient Co-Administration with Rapamycin," Journal of Thrombosis and Haemostasis, 2011, pp. 1524-1533, vol. 9.

Peng, Y. et al., "Innate and Adaptive Immune Response to Apoptotic Cells," Journal of Autoimmunity, 2007, pp. 303-309, vol. 29.

(56) References Cited

OTHER PUBLICATIONS

Pratt, K.P., "Inhibitory Antibodies in Hemophilia A," Curr Opin Hematol, Sep. 2012, pp. 399-405, vol. 19, No. 5.
Qadura, M. et al., "Reduction of the Immune Response to Factor VIII Mediated Through Tolerogenic Factor VIII Presentation by Immature Dendritic Cells," Journal of Thrombosis and Haemostasis, 2008, pp. 2095-2104, vol. 6.
Qian, J. et al., "Prevention and Treatment of Factor VIII Inhibitors in Murine Hemophilia A," Blood, 2000, pp. 1324-1329, vol. 95.
Ragni, M.V. et al., "Factor VIII-Pulsed Dendritic Cells Reduce Anti-Factor VIII Antibody Formation in the Hemophilia A Mouse Model," Experimental Hematology, 2009, pp. 744-754, vol. 37.
Rawle, F.E. et al., "Induction of Partial Immune Tolerance to Factor VIII Through Prior Mucosal Exposure to the Factor VIII C2 Domain," Journal of Thrombosis and Haemostasis, 2006, pp. 2172-2179, vol. 4.
Reipert, B.M. et al., "Blockade of CD40/CD40 Ligand Interactions Prevents Induction of Factor VIII Inhibitors in Hemophilic Mice but Does Not Induce Lasting Immune Tolerance," Thromb. Haemost., 2001, pp. 1345-1352, vol. 86.
Rossi, G. et al., "Long-Term Induction of Immune Tolerance After Blockade of CD40-CD40L Interaction in a Mouse Model of Hemophilia A," Blood, 2001, pp. 2750-2757, vol. 97.
Su, R.J. et al., "Suppression of FVIII Inhibitor Formation in Hemophilic Mice by Delivery of Transgene Modified Apoptotic Fibroblasts," Molecular Therapy, Jan. 2010, pp. 214-222, vol. 18.
Walker, S.M. et al., "In Vitro Tolerance Induction of Primed, IgD-Negative Murine Spleen Cells," J Exp Med, 1981, pp. 653-664, vol. 153.
Waters, B. et al., "Anti-CD3 Prevents Factor VIII Inhibitor Development in Hemophilia A Mice by a Regulatory CD4+CD25+-Dependent Mechanism and by Shifting Cytokine Production to Favor a Th1 Response," Blood, Jan. 1, 2009, pp. 193-203, vol. 113, No. 1.
Weigle, W.O. "Immunological Unresponsiveness," Adv. Immunol., 1973, pp. 61-122, vol. 16.
Wu, H. et al., "Mechanism of the Immune Response to Human Factor VIII in Murine Hemophilia," Thromb Haemost, 2001, pp. 125-133, vol. 85.
Zehn, D. et al., "T Cells with Low Avidity for a Tissue-Restricted Antigen Routinely Evade Central and Peripheral Tolerance and Cause Autoimmunity," Immunity, Aug. 2006, pp. 261-270, vol. 25.
Chace, J.H. et al., "Effect of Anti-CD4 on CD4 Subsets: I. Anti-CD4 Preferentially Deletes Resting, Naive CD4 Cells and Spares Activated CD4 Cells," Journal of Immunology, 1994, pp. 405-412, vol. 152.
Cho, B.K. et al., "Functional Differences Between Memory and Naive CD8 T Cells," Proc.Natl. Acad. Sci. USA, Mar. 1999, pp. 2976-2981, vol. 96.
Lakkis, F.G. et al., "Memory T Cells: a Hurdle to Immunologic Tolerance," J. Am. Soc. Nephrol., 2003, pp. 2402-2410, vol. 14.
Larsen, C.P. et al., "CD40-gp39 Interactions Play a Critical Role During Allograft Rejection: Suppression of Allograft Rejection by Blockade of the CD40-gp39 Pathway," Transplantation, Jan. 15, 1996, pp. 4-9, vol. 61, No. 1.
Parker, D.C. et al., "Survival of Mouse Pancreatic Islet Allografts in Recipients Treated with Allogeneic Small Lymphocytes and Antibody to CD40 Ligand," Proc. Natl. Acad. Sci. USA, Oct. 1995, pp. 9560-9564, vol. 92.
Propper, D.J. et al., "The Effects of Rapamycin on Humoral Immunity In Vivo: Suppression of Primary Responses but Not of Ongoing Alloantibody Synthesis or Memory Responses," Transplantation, Dec. 1992, pp. 1058-1063, vol. 54, No. 6.
Ranges, G.E. et al., "In Vivo Immunomodulation by Monoclonal Anti-L3T4: 1. Effects on Humoral and Cell-Mediated Immune Response," Cellular Immunology, 1987, pp. 163-173, vol. 106.
Ranges, G.E. et al., "Prevention of Type II Collagen-Induced Arthritis by In Vivo Treatment with Anti-L3T4," J. Exp. Med., Sep. 1985, pp. 1105-1110, vol. 162.
Zhai, Y. et al., "Allograft Rejection by Primed/Memory CD8+ T Cells is CD154 Blockade Resistant: Therapeutic Implications for Sensitized Transplant Recipients," The Journal of Immunology, 2002, pp. 4667-4673, vol. 169.

* cited by examiner

A

B

C

A

B

C

A

B

A

B

A

B

A

B

SUPPRESSION OF IMMUNE RESPONSE TO FACTOR VIII IN HEMOPHILIA A PATIENTS

CROSS REFERENCE TO RELATED APPLICATION

This application claims the benefit of U.S. Provisional Application No. 61/159,021 filed Mar. 10, 2009, which is hereby incorporated in its entirety by reference.

FIELD OF THE INVENTION

Provided herein are methods and compositions for suppressing an immune response to Factor VIII in subjects suffering from hemophilia A, and in particular in subjects having preformed inhibitor antibodies against Factor VIII. The compositions and methods advantageously render subjects amenable to standard treatments for hemophilia A, including Factor VIII replacement therapy.

BACKGROUND OF THE INVENTION

Factor VIII (FVIII) is a protein found in blood plasma which acts as a cofactor in the cascade of reactions leading to blood coagulation. A deficiency in the amount of FVIII activity in the blood results in the clotting disorder known as hemophilia A, which is primarily a congenital condition but can also be acquired in rare cases. Hemophilia A is currently treated with therapeutic preparations of FVIII derived from human plasma or manufactured using recombinant DNA technology. FVIII can be administered in response to a bleeding episode (on-demand therapy) and/or at frequent, regular intervals to prevent uncontrolled bleeding (prophylaxis).

Up to 30% of patients with severe hemophilia A (FVIII activity <1%) develop inhibitory antibodies to FVIII as a consequence of treatment with therapeutic preparations of FVIII (Lusher et al., J Thromb Haemost; 2:574-583 (2004); Scharrer et al., Haemophilia; 5:145-154 (1999)). Frequently, the inhibitors are persistent and of sufficiently high titer that infusion of FVIII concentrates is ineffective for controlling bleeding episodes. Inhibitor formation therefore represents a major obstacle in treating patients with hemophilia A. In patients with high titer inhibitors, acute bleeding can sometimes be controlled by infusion of bypass clotting factors, including activated prothrombin complex concentrates and recombinant human Factor VIIa. Bypass factors are considerably more expensive than standard FVIII concentrates, and their use in long-term prophylaxis regimens is limited due to their thrombogenic potential and unreliable hemostatic profile (Hay et al., Br J Haematol; 133:591-605 (2006); Paisley et al., Haemophilia; 9:405-417 (2003)). As a result, patients with high titer inhibitors have a markedly reduced quality of life due to frequent joint bleeds and the early progression of arthropathies (Morfini et al., Haemophilia; 13:606-612 (2007)).

At present, the only effective clinical protocols for immune tolerance induction (ITI) to FVIII involve daily administration of FVIII concentrate over the course of many months to 2 years. Administration of large quantities of soluble antigens has long been known to induce non-responsiveness to subsequent immunological challenge, but the high doses required and the inconsistency of tolerance induction make antigen administration alone impractical for most therapeutic agents. For example, ITI using FVIII is expensive, with a cost of approximately $1 million per treated patient (Colowick et al., Blood; 96:1698-1702 (2000)), and the mechanism by which it works is unknown. ITI is effective 60-80% of the time (Dimichele, J Thromb Haemost; 5 Suppl 1:143-150 (2007)) and its high costs can be offset by projected reductions in patient mortality and total lifetime treatment costs (Colowick et al., Blood; 96:1698-1702 (2000)). However, the morbidity and mortality suffered by patients with high titer FVIII inhibitors, the significant expense and high (20-40%) failure rate of current ITI protocols, and the extreme financial cost and limited effectiveness of alternative hemostatic agents all underscore the need to develop quicker, more reliable, and less expensive methods for tolerance induction.

Studies have shown that autologous cells undergoing apoptosis in the normal course of tissue turnover (under steady state conditions) are processed by unactivated dendritic cells (DCs) which phagocytose the apoptotic cells (ACs) and present AC antigens in the context of MHC Class I and II molecules to regulatory T cells capable of mediating antigen specific tolerance (Peng et al., J Autoimmun 29:303-309, (2007)). Regulatory T cells act to generate antigen specific tolerance through a variety of mechanisms including down regulation of DC activation, competition with effector T cells for access to antigen on DCs, and direct suppression of effector T cell proliferation by cytokine mediated inhibition or through Fas-Fas ligand cytolytic deletion (Misra et al., J Immunol; 172:4676-4680 (2004); Zhang et al.; Nat Med; 6:782-789 (2000); Vigoroux et al.; Blood; 104:26-33 (2004); Rutella et al.; Immunol Lett; 94:11-26 (2004)) Further research has shown that the immune response to a foreign antigen can also be suppressed by delivering it systemically in association with syngeneic ACs (Liu et al., J Exp Med; 196: 1091-1097 (2002); Ferguson et al., J Immunol; 168:5589-5595 (2002)). In contrast, immunity rather than tolerance was stimulated against AC-associated antigens when ACs were processed by DCs in the presence of an activation signal provided by an agonistic anti-CD40 antibody (Liu et al. (2002)). Thus, antigen presentation by DCs can lead to either immune priming or tolerance induction; it is the activation state of the DCs that process and present the antigen that determines the fate of the subsequent immune response (IR) (Moser, Immunity; 19:5-8 (2003); Probst et al., Immunity; 18:713-720 (2003)).

DCs exist in multiple phenotypically distinct subpopulations. Tolerogenic DCs are unactivated, expressing low levels of the T cell costimulatory molecules CD80 and CD86 and MHC Class II. These DCs also do not secrete pro-inflammatory cytokines such as IL-12, TNF-α, and IL1-β and therefore lack the ability to stimulate effector T cells. In contrast, tolerogenic DCs generate anti-inflammatory cytokines such as IL-10 that prevent immune priming of effector T cells and provide autocrine signals serving to keep DCs relatively resistant to activation (Sauter et al., J Exp Med; 191:423-434 (2000); Steinman et al., Annu Rev Immunol; 21:685-711 (2003); Stuart et al., J Immunol; 168:1627-1635 (2002)). Thus, the processing of autologous ACs by unactivated tolerogenic DCs does not produce an immune priming response, allowing for the induction of tolerance to AC-associated antigens.

ACs are more than just passive participants in this process. After phagocytosing ACs, immature DCs become more resistant to maturation and activation, in part due to blockade of NF-κB activation (Sen et al., Blood; 109: 653-660 (2007); Stuart et al., J Immunol; 168:1627-1635 (2002)). Furthermore, phagocytes that ingest ACs show decreased production of proinflammatory cytokines including IL-12, TNF-α, and IL1-β along with increased generation of the anti-inflammatory cytokine IL-10 (Kim et al., Immunity; 21:643-653 (2004); Voll et al., Nature; 390:350-351 (1997)). ACs also release their own anti-inflammatory signals, such as transforming growth factor (TGF)-β (Chen et al., Immunity; 14:715-725 (2001)), which may inhibit effector T cells at the sites of antigen processing and presentation.

The ability to induce peripheral tolerance by presenting antigens in association with apoptotic cells suggests that such cells might be useful vehicles for administering FVIII to prevent generation of high titer anti-FVIII inhibitory antibodies. To this end, a syngeneic fibroblast cell line was developed from an FVIII knockout (KO) mouse, and the cells were transduced with a vector expressing a human FVIII construct (Su et al., Blood (ASH Annual Meeting Abstracts); 106: 216 (2005); Su et al., Blood (ASH Annual Meeting Abstracts); 108: 768 (2006)). The transduced cells were induced to undergo apoptosis and then administered to FVIII KO mice prior to immunization with 4 doses of recombinant human FVIII. Mice that received apoptotic cells expressing the FVIII construct had reduced inhibitor titers and T cell responses compared to controls (Su et al. (2005); Su et al. (2006)). However, mice that were re-challenged with additional doses of rhFVIII 4 months after the initial immunization all showed significant boosting of the titers of inhibitory antibodies to FVIII (Su et al. (2006)). Thus the initial suppression of the immune response to FVIII by the vector modified apoptotic fibroblasts did not result in durable tolerance. Furthermore, the findings of Su et al. were limited to subjects that were immunologically naive to FVIII. Thus, the studies did not address whether the methods might be applicable to subjects having preformed immune responses to FVIII, such as the large population of hemophilia A patients who have developed high titer inhibitors to FVIII as a consequence of therapeutic infusions of FVIII concentrates.

Accordingly, there is a need in the art for safe, effective, and low cost treatments for hemophilia A patients with inhibitors to FVIII, as well as hemophilia A patients that are immunologically naive to FVIII.

SUMMARY OF THE INVENTION

Methods are provided herein for suppressing an immune response to Factor VIII (FVIII) and treating hemophilia A, where the methods comprise administering apoptotic cells containing recombinant DNA encoding an FVIII polypeptide to a subject suffering from hemophilia A. In some preferred aspects, the subject has a preformed inhibitor response to FVIII. In further aspects, administering the apoptotic cells is effective to induce immunological tolerance to FVIII. In some aspects, administering the apoptotic cells is effective to induce immunological tolerance to a therapeutically effective amount of a biologically active FVIII polypeptide. In various aspects, administering the apoptotic cells can comprise a single administration or multiple (e.g., one, two, three, four, five, or more) administrations of the cells.

In some aspects, methods are provided for suppressing an immune response to FVIII, comprising the steps of (a) transfecting or transducing cells with an expression vector encoding a tolerogenic FVIII polypeptide, where the cells are syngeneic with a subject suffering from hemophilia A with inhibitors to FVIII; (b) inducing apoptosis in the cells; and (c) administering the apoptotic cells to the subject, wherein administering the apoptotic cells is effective to induce immunological tolerance to FVIII.

In some aspects, methods are provided for suppressing an immune response to FVIII, comprising the steps of (a) transfecting or transducing cells with an expression vector encoding a tolerogenic FVIII polypeptide; (b) inducing apoptosis in the cells; and (c) administering the apoptotic cells to the subject, wherein administering the apoptotic cells is effective to induce immunological tolerance to FVIII.

In further aspects, methods are provided for treating hemophilia A, comprising administering apoptotic cells containing an expression vector encoding a tolerogenic FVIII polypeptide to a subject suffering from hemophilia A with inhibitors to FVIII, where the cells are syngeneic with the subject and effective to induce immunological tolerance to FVIII; and administering a therapeutically effective amount of a biologically active FVIII polypeptide to the subject.

In further aspects, methods are provided for treating hemophilia A, comprising administering apoptotic cells containing an expression vector encoding a tolerogenic FVIII polypeptide to a subject suffering from hemophilia A with inhibitors to FVIII, where the cells are effective to induce immunological tolerance to FVIII; and administering a therapeutically effective amount of a biologically active FVIII polypeptide to the subject.

In some aspects, administering the apoptotic cells to the subject comprises separately administering two or more doses of the apoptotic cells, each dose being administered on a different day. In further aspects, administering the apoptotic cells to the subject comprises separately administering four or more doses of the apoptotic cells, each dose being administered on a different day.

In some aspects, the subject has endogenous FVIII activity of 10% or less, or 5% or less, or 2% or less, or 1% or less than normal. In further aspects, the subject has high responding inhibitors to FVIII.

In some aspects, the subject is resistant to established methods of inducing immunological tolerance to FVIII. In some aspects, the subject is resistant to the induction of immunological tolerance by administering an FVIII polypeptide in substantially purified form.

In various aspects, the immunological tolerance to FVIII is associated with a Bethesda titer of 5 or less, or 3 or less, or 1 or less. In further aspects, the immunological tolerance to FVIII is associated with a decrease of at least 50%, or at least 65%, or at least 80% in Bethesda titer.

In some aspects, the immunological tolerance to FVIII can be adoptively transferred to naive subjects.

In some aspects, the apoptotic cells are syngeneic apoptotic cells. In further aspects, the syngeneic apoptotic cells are autologous with the subject. In some aspects, the syngeneic apoptotic cells are harvested from an immunologically compatible donor.

In some aspects, the apoptotic cells are dermal fibroblasts. In other aspects, the apoptotic cells are mesenchymal stem cells.

In some aspects, the tolerogenic FVIII polypeptide comprises a fragment of an FVIII polypeptide. In some aspects, the tolerogenic FVIII polypeptide comprises at least one immunodominant T cell epitope of an FVIII polypeptide. In some aspects, the immunodominant T cell epitope is an epitope known to stimulate an immune response against FVIII by presentation on MHC class II.

In some aspects, the expression vector encoding the tolerogenic FVIII polypeptide further encodes one or more additional proteins. In some aspects the one or more additional proteins comprises an anti-inflammatory cytokine. In some aspects, the anti-inflammatory cytokine is selected from interleukin-10 (IL-10) and transforming growth factor-β (TGF-β). In some aspects, the one or more additional proteins comprises a protein that modulates the expression and/or activity of a cytokine.

In some aspects, apoptosis is induced by exposing the syngeneic cells to an apoptosis-inducing amount of UV irradiation. In some preferred aspects, the apoptosis-inducing amount of UV irradiation is effective to induce apoptosis in the absence of substantial necrosis.

In some aspects, apoptosis is induced by exposing the cells to an apoptosis-inducing amount of UV irradiation. In some preferred aspects, the apoptosis-inducing amount of UV irradiation is effective to induce apoptosis in the absence of substantial necrosis.

In some aspects, methods provided herein further comprise administering an antagonist of the CD40-CD40 ligand interaction. In some aspects, the antagonist is a blocking monoclonal anti-CD40 antibody and in some aspects the antagonist is an anti-CD40 ligand antibody.

In yet further aspects, pharmaceutical compositions are provided herein, comprising apoptotic cells and a pharmaceutically acceptable excipient, where the apoptotic cells are syngeneic with a subject suffering from hemophilia A and contain an expression vector encoding a tolerogenic FVIII polypeptide. In some aspects, the composition comprises an amount of the apoptotic cells effective to induce immunological tolerance to FVIII.

In yet further aspects, pharmaceutical compositions are provided herein, comprising apoptotic cells and a pharmaceutically acceptable excipient, where the apoptotic cells contain an expression vector encoding a tolerogenic FVIII polypeptide. In some aspects, the composition comprises an amount of the apoptotic cells effective to induce immunological tolerance to FVIII.

In still further aspects, kits for inducing immunological tolerance to FVIII are provided herein, comprising a container holding an expression vector encoding a tolerogenic FVIII polypeptide; and instructions for (a) transfecting or transducing cells with the expression vector, where the cells are syngeneic with a subject suffering from hemophilia A with inhibitors to FVIII, (b) inducing apoptosis in the vector modified cells, and (c) administering the cells to the subject in an amount effective to induce immunological tolerance to FVIII.

In still further aspects, kits for inducing immunological tolerance to FVIII are provided herein, comprising a container holding an expression vector encoding a tolerogenic FVIII polypeptide; and instructions for (a) transfecting or transducing cells with the expression vector, (b) inducing apoptosis in the vector modified cells, and (c) administering the cells to the subject in an amount effective to induce immunological tolerance to FVIII.

BRIEF DESCRIPTION OF THE DRAWINGS

FIG. 6 is a graph showing Bethesda titers in preimmunized hemophilic mice after dosing with UV irradiated Fibro/IZ or Fibro/F8IZ cells. Two weeks after completing immunization with four weekly doses of rhFVIII, mice were given 2-6 weekly infusions of UV-irradiated Fibro/IZ or Fibro/F8IZ cells. The analysis was performed one week after delivery of the last dose of ACs.

DETAILED DESCRIPTION

Figure 1:
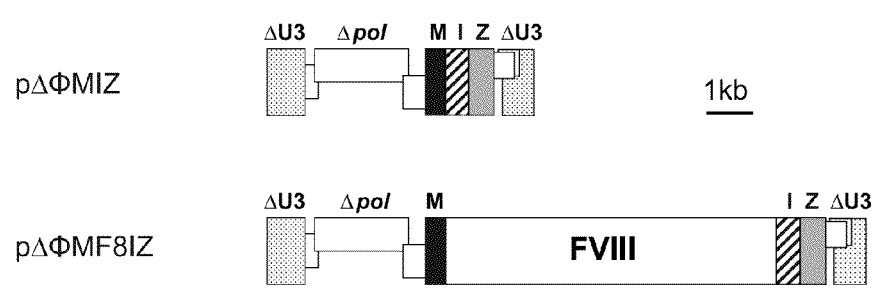
FIG. 1A is an illustration of the foamy virus vectors ΔΦMIZ and ΔΦMF8IZ that contain the murine stem cell virus promoter (M), an internal ribosomal entry site (I) and the zeocin resistance gene (Z).
FIG. 1B is a Western analysis of human FVIII protein in cell lines.
FIG. 1C is an immunofluorescent intracellular staining of human FVIII in Fibro/IZ (shaded histogram) and Fibro/F8IZ (open histogram) cells.
Figure 1:
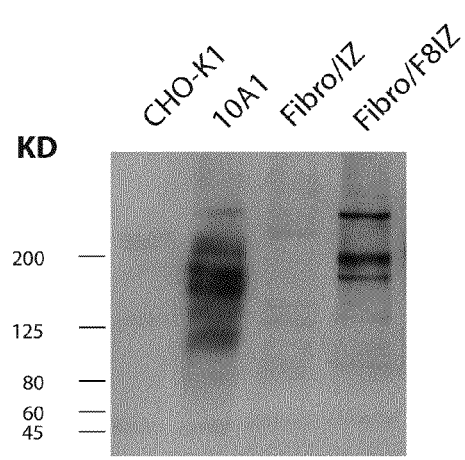
Figure 1:
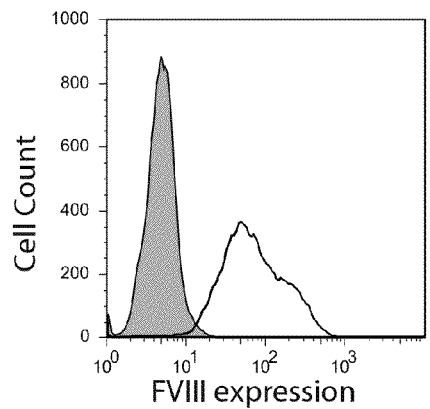

Descriptions of the invention are presented herein for purposes of describing various aspects, and are not intended to be exhaustive or limiting, as the scope of the invention will be limited only by the appended claims. Persons skilled in the relevant art can appreciate that many modifications and variations are possible in light of the aspect teachings.

Unless defined otherwise, all technical and scientific terms used herein have the meaning commonly understood by one of ordinary skill in the art to which this invention belongs. While exemplary methods and materials are described herein, it is understood that methods and materials similar or equivalent to those described can be used. All publications mentioned herein are incorporated by reference to disclose and describe the methods and/or materials in connection with which they are cited.

It must be noted that, as used in the specification, the singular forms "a," "an" and "the" include plural referents unless the context clearly dictates otherwise.

Methods are provided herein for suppressing an immune response to FVIII in a subject suffering from hemophilia A by administering apoptotic cells to the subject which have been modified to express an FVIII transgene. Prior studies have shown that administering FVIII within syngeneic apoptotic cells (ACs) can prevent an adaptive immune response to FVIII in subjects that are immunologically naive to the antigen.

Without being limited to a particular theory, it is believed that apoptotic cells administered to naive subjects are phagocytosed by unactivated tolerogenic dendritic cells (DCs) that inhibit an adaptive immune response to the antigen through a variety of mechanisms, including, e.g., cross-priming of antigen specific regulatory T cells, clonal deletion of effector T cells, and anergy induction. However, studies have also shown that ACs that induce tolerance under steady state conditions stimulate immunity rather than tolerance against AC-associated antigens when administered in the presence of a stimulatory signal, such as that provided by a CD40 ligand or by an agonistic anti-CD40 antibody. Some anti-CD40 antibodies mimic signaling by CD40 ligand (CD40L) and are used to substitute for the function of CD4$^+$ lymphocytes in the activation of dendritic cells (DCs) (e.g., Bennett et al., Nature; 393:478-80 (1998)). Since subjects with preformed immune responses against FVIII would be expected to have an expanded population of effector CD4$^+$ lymphocytes specific for FVIII antigens, administering ACs expressing FVIII to non-naive subjects would be expected to stimulate an immune response rather than tolerance to FVIII. Furthermore, since the effects of delivering FVIII vector expressing apoptotic fibroblasts were short-lived in naive mice, and overcome by additional antigen exposure, it was not expected that treatment with these cells would be able to suppress a robust pre-formed immune response to FVIII.

The instant invention is related to the surprising discovery that apoptotic fibroblasts which express an FVIII transgene are capable of suppressing the immune response to FVIII not only in naive subjects, but also in subjects having a preformed immune response to FVIII. Thus, the instant methods are useful for treating hemophilia A patients with FVIII inhibitors, including patients with inhibitors to FVIII developed through prior FVIII replacement therapy.

The term "subject" is understood to include any animal, including but not limited to a human or a veterinary subject, such as a primate, a dog, a cat, a horse, a cow, and the like, having an FVIII deficiency. An "FVIII deficiency" includes any deficiency in clotting activity caused by insufficient FVIII activity, for example due to production of a defective Factor VIII, inadequate production of FVIII, or partial or total inhibition of FVIII by inhibitors. The level of FVIII in normal humans fluctuates in response to various physiologic and non-physiologic stimuli, and can be defined as a range centered around a mean level (e.g., determined in a sample plasma pool derived from a statistically significant number of normal donors). In some aspects, the normal FVIII level is between 50-200% of the mean FVIII level. Subjects having an FVIII deficiency typically have a congenital form of hemophilia A, but they can also have "acquired hemophilia," a condition in which normal individuals spontaneously develop inhibitory antibodies to FVIII, creating an FVIII deficiency.

The term "syngeneic" refers to the property of being genetically and/or antigenetically similar. Syngeneic samples are optionally autologous. The term "autologous" refers to the property of being derived from the same organism.

Hemophilia occurs in all degrees of severity. Patients with no detectable FVIII or less than 1% of a normal level of FVIII are usually severely affected and bleed into muscles and joints upon minimal trauma and/or spontaneously. A small amount of FVIII gives considerable protection, such that patients with 1-5% of normal levels usually suffer only posttraumatic bleeding and less severe bleeding into muscles and joints, etc., and can be classified as moderately affected. Patients with more than 5% of Factor VIII usually bleed only after significant trauma or surgery and can be classified as mildly affected. It must be realized, however, that this classification is not always valid in individual cases. For example, some patients with very low Factor VIII levels rarely bleed while others having over 5% FVIII activity may bleed repeatedly into a "target joint" damaged by prior trauma and appear to be "severely" affected. As a general matter, however, bleeding symptoms are less apparent with higher factor levels so that abnormal bleeding does not usually occur at Factor VIII levels over 35-40% of normal levels.

In some preferred aspects, the subject has severe hemophilia A, with FVIII activity of less than 5% of normal levels, or more preferably less than 2% of normal levels, or even more preferably less than 1% of normal levels. FVIII can be assayed for immunoreactivity and coagulation activity using methods known in the art, such as the one-stage clotting assay (Doering et al., J. Biol. Chem.; 277: 38345-38349 (2002)), the plasma-free FVIII assay, or ELISA, using purified recombinant human FVIII as a standard. The blood coagulation activity (potency) of FVIII is typically measured in International Units (IU). Chromogenic assays may be purchased commercially, such as Coatest Factor VIII, available from Chromogenix AB, Molndal, Sweden.

In various preferred aspects, the subject has a preformed immune response to FVIII that includes antibodies that inhibit the coagulant activity of FVIII (FVIII "inhibitors"). Inhibitors can interfere with FVIII activity through any mechanism, including for example disruption of intramolecular interactions within one or more domains of FVIII and/or disruption of intermolecular associations between FVIII and, e.g., von Willebrand factor, thrombin, Factor Xa, Factor IXa, or Factor X. FVIII inhibitor titers can be measured using the Bethesda assay (Kasper et al., Thromb. Diath. Haemorrh., 34: 869-872 (1975)), in which recombinant FVIII is added to hemophilia A plasma and incubated with varying concentrations of inhibitor for 2 hours at 37° C. One Bethesda unit (BU) is defined as the amount of inhibitor activity that produces 50% inhibition of FVIII activity in the one-stage clotting assay.

Subjects having a Bethesda titer against FVIII of <5 are generally considered to have "low titer" inhibitors, whereas subjects with a Bethesda titer of >5 are generally considered to have "high titer" inhibitors. For patients with high titer inhibitors, FVIII replacement therapy is usually partially or wholly ineffective. Thus, in some preferred aspects, methods provided herein induce tolerance in a subject having high titer inhibitors against FVIII. In some aspects, methods provided herein induce tolerance in high titer subjects that are resistant to standard methods of immunological tolerance induction (ITI) (e.g., involving prolonged administration of large doses of FVIII in a substantially purified form). In further aspects, methods provided herein are used to induce tolerance in a subject having low titer inhibitors, such as low titer subjects for which FVIII replacement therapy is partially or wholly ineffective, and/or low titer subjects for which improving the cost and/or efficacy of FVIII replacement therapy would otherwise be beneficial.

In various aspects, methods and compositions provided herein are effective in suppressing an immune response to FVIII. In some aspects, methods and compositions provided herein are effective in inducing immunological tolerance to FVIII. In some preferred aspects, methods and compositions provided herein are effective in inducing immunological tolerance to FVIII in hemophilia A subjects with inhibitors against FVIII. In further aspects, the methods and compositions are effective in inducing immunological tolerance to FVIII in subjects who are resistant to standard FVIII replacement therapies and/or established protocols for ITI against FVIII.

In some aspects, methods and compositions provided herein are effective in inducing immunological tolerance to a therapeutically effective amount of FVIII. A "therapeutically effective amount of FVIII" is an amount of a biologically active FVIII polypeptide that, when administered to a subject having an FVIII deficiency, achieves a level of FVIII activity in the subject that is sufficient to produce a measurable improvement in one or more symptoms of hemophilia A or a protective effect in the subject (e.g., to prevent, stop and/or control bleeding). Thus, in some aspects, "immunological tolerance" connotes an absence of an immune response which substantially interferes with the alleviation of hemophilia A symptoms in the subject upon administration of a therapeutically effective amount of FVIII, e.g., via established methods of providing FVIII replacement therapy.

General guidelines for FVIII replacement therapy are known in the art, and are described, e.g., in Roberts and Jones, "Hemophilia and Related Conditions—Congenital Deficiencies of Prothrombin (Factor II, Factor V, and Factors VII to XII)," Ch. 153: 1453-1474, 1460, in Hematology, Williams et al., ed. (1990). While it is understood that specific dosage regimens should be adjusted according to the individual needs of the particular subject and the professional judgment of the person supervising the treatment, the following ranges provide exemplary guidelines for FVIII replacement therapy in accordance with methods described herein. Such guidelines are not intended to limit the scope or practice of the claimed invention.

In some aspects, a therapeutically effective amount of FVIII is an amount that achieves at least 20%, or preferably at least 25%, or more preferably at least 30% of normal FVIII activity. As a general, non-limiting guideline, a therapeutically effective amount of FVIII may be given intravenously at a dosage range of about 5 to 50 units/kg body weight, or more preferably at a range of 10-50 units/kg body weight, or even more preferably at a dosage range of about 20-40 units/kg body weight. In further aspects, the interval frequency is in the range from about 8 to 24 hours, and the duration of treatment is in the range of about 1 to 10 days or until the bleeding episode is resolved. In some preferred aspects, the effective amount of FVIII (adjusted for activity level of the FVIII preparation) for replacement therapy in subjects who have been administered a tolerogenic composition according to methods provided herein is significantly less than the effective amount prior to the induction of tolerance. For example, in various aspects, the effective amount is at least 30% less, or preferably at least 50% less, or more preferably at least 75% less than the effective amount prior to the induction of tolerance.

FVIII preparations useful in FVIII replacement therapy can either be plasma derived or obtained using recombinant techniques well known in the art. Commercially available preparations of FVIII include those sold under the trade names of HEMOFIL M®, ADVATE®, and RECOMBINATE™ (available from Baxter Healthcare Corporation, Deerfield, Ill., U.S.A.). HEMOFIL M is a plasma-derived purified factor product, while ADVATE and RECOMBINATE are recombinant factor products. Other commercial preparations of FVIII may lack all or part of the B domain portion of the molecule.

FVIII exists naturally and in therapeutic preparations as a heterogeneous distribution of polypeptides arising from a single gene product (e.g., Andersson et al., Proc. Natl. Acad. Sci. USA, 83, 2979-2983 (1986)). "Factor VIII" or "FVIII" refers to all such polypeptides, whether derived from blood plasma or produced through the use of recombinant DNA techniques or by other means.

FVIII is secreted as an approximately 300 kDa single chain glycoprotein having the following domain organization $NH_2$-A1-A2-B-A3-C1-C2-COOH, where each "domain" comprises a structural unit encoded by a continuous sequence of amino acids. FVIII isolated from plasma comprises two subunits, known as the heavy chain and light chain. The FVIII heavy chain comprises the A1, A2, and B domains, and the FVIII light chain comprises the A3, C1, and C2 domains. The B domain has no known biological function in clot formation and can be wholly or partially removed without significantly altering FVIII function.

FVIII is usually complexed with another plasma protein, von Willebrand factor (vWF), which is present in a large molar excess to FVIII in plasma and protects FVIII from premature degradation by plasma proteases. FVIII is proteolytically activated by thrombin (Factor IIa), which cleaves the heavy chain between the A1 and A2 domains and dissociates FVIII from von Willebrand factor (vWF) to form Factor VIIIa (FVIIIa), which is the active form of FVIII having coagulant activity. FVIIIa acts as a co-factor of activated Factor IX, which accelerates the activation of Factor X, which converts prothrombin into thrombin, which converts fibrinogen into fibrin, which induces clotting.

In various aspects, methods provided herein involve administering apoptotic cells that have been modified to express an FVIII transgene. The methods generally involve harvesting cells from a donor source, culturing the cells, and transducing or transfecting the cells with a vector comprising a nucleic acid sequence encoding a tolerogenic FVIII polypeptide. In some aspects, the amino acid sequence of the tolerogenic FVIII polypeptide is identical to all or a portion of the amino acid sequence of an FVIII polypeptide that will be used in replacement therapy after tolerance has been induced.

"Primary cells" include cells isolated from a donor tissue source (prior to being plated), cells present in a tissue explant, cells plated for the first time and cell suspensions derived from such cells. "Secondary cells" include cells at all subsequent steps in culturing. A cell strain consists of secondary cells that: 1) have been passaged one or more times; 2) exhibit a finite number of mean population doublings in culture; 3) exhibit the properties of contact-inhibited, anchorage dependent growth; and 4) are not immortalized. A "clonal cell strain" is derived from a single founder cell, whereas a "heterogeneous cell strain" is derived from two or more founder cells.

Primary and secondary cells can be obtained from a variety of tissues and include all cell types which can be maintained and propagated in culture, such as fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells, other somatic cells which can be cultured, and precursors of these somatic cell types. Primary cells are preferably syngeneic with respect to the subject. In various aspects, the syngeneic cells can be autologous cells (cells obtained from the subject to whom the transfected or transduced cells are to be administered, or cells derived from such cells). The cells can also be allogeneic cells from immunologically compatible donors (e.g., from an HLA-matched donor, such as a sibling or other relative), or allogeneic cells from other donor sources (e.g., embryonic, neonatal, and/or adult stem cells or progenitor cells). In some preferred aspects, the primary cells are autologous hematopoietic cells, thymocytes, splenocytes, lymphocytes, monocytes, fibroblasts, keratinocytes, or combinations thereof. In further preferred aspects, the primary cells are autologous or allogeneic mesenchymal stem cells or progenitor cells.

Tissues and cells can be harvested from an appropriate donor using known procedures, including but not limited to, biopsy, aspiration, and lavage procedures. For example, punch biopsy can be used to obtain skin as a source of fibroblasts or keratinocytes. A mixture of primary cells can be obtained from harvested tissue using known methods, such as enzymatic digestion (e.g., using collagenase, hyaluronidase, dispase, pronase, trypsin, elastase, and chymotrypsin) or explantation, and cell types of interest can be isolated using methods known in the art, such as FACS (fluorescence activated cell sorting).

Primary or secondary cells are transfected or transduced with an expression vector comprising an exogenous nucleic acid encoding a tolerogenic FVIII polypeptide. An "expression vector" is a DNA element capable of replicating autonomously in a host cell and/or integrating into a host cell genome and possessing additional control sequences which permit expression of a coding DNA sequence of interest. Expression vectors useful in methods provided herein typically have, in the 5'-3'-direction of transcription, a transcriptional initiation and translational initiation region, a structural gene sequence coding for FVIII, and translational and transcriptional termination sequences. The initiation region may comprise a number of sequence elements, such as enhancer sequences, RNA polymerase binding sites, RNA capping sites, ribosomal binding and translational initiation sites, and the like. Examples of initiation regions known to be operative in mammalian host cells include, but are not limited to, the SV40 early promoter and late promoter regions, the adenovirus major late promoter region, actin promoter region, the cytomegalovirus $M_r$ 72 K immediate early protein promoter region, the metallothionein promoter, and the like. The termination region may include 3'-untranslated sequences, a polyadenylation signal sequence, and the like.

Vectors suitable for use in the instant methods can be viral or non-viral. In some preferred aspects, the vector is a viral vector, such as an adenovirus vector, an adeno-associated virus vector, a herpes simplex virus vector, a foamy virus vector, a lentivirus vector, a retrovirus vector, or the like. A non-viral vector, such as a plasmid may also be used in the instant methods and compositions.

A variety of methods are known in the art for recombinantly engineering expression constructs containing a nucleic acid of interest, and replicating and expressing the nucleic acid in a suitable host. For example, general recombinant DNA methodology is described in Sambrook et al., 1989, MOLECULAR CLONING: A LABORATORY MANUAL, Cold Spring Harbor Laboratory (New York); and Ausubel et al., CURRENT PROTOCOLS IN MOLECULAR BIOLOGY, 1997, John Wiley & Sons (New York). A variety of vectors, including both plasmid and viral vectors, are known to be suitable for expressing a recombinant gene construct in eukaryotic cells (see, for example, Sambrook et al., Chapter 16). Other vectors and expression systems, including bacterial, yeast, and insect cell systems, can be used but are not preferred due, e.g., to differences in glycosylation and/or other post-translational modifications.

The tolerogenic FVIII polypeptide encoded by the expression vector may comprise the full-length FVIII amino acid sequence or any portion thereof sufficient to induce immunological tolerance to FVIII in the subject. The cDNA sequence encoding human FVIII and its predicted amino acid sequence are shown in SEQ ID NOs: 1 and 2, respectively. In some aspects, Factor VIII is modified to delete part or all of the B domain, as described, e.g., in U.S. Pat. No. 4,868,112. The tolerogenic FVIII polypeptide need not have coagulant activity, and need not be expressed and/or secreted by the apoptotic cells at levels necessary for FVIII replacement therapy (at levels required for gene therapy). In some aspects, a therapeutically effective amount of FVIII (e.g., a commercial preparation of substantially purified FVIII) is administered to provide FVIII replacement therapy after immunological tolerance to FVIII is induced by administering apoptotic cells as described herein.

In some preferred aspects, the tolerogenic FVIII polypeptide comprises one or more T cell epitopes. T cell epitopes are short antigenic peptides presented by major histocompatibility complex (MHC) receptors on the surfaces of antigen-presenting cells (APCs), such as dendritic cells, macrophages, and B cells. MHC surface receptors display both self antigens and non-self (foreign) antigens, which are recognized by T cell receptors (TCRs) on the surfaces of T cells. Without being bound by a particular theory, it is believed that syngeneic apoptotic cells can be phagocytosed by a population of tolerogenic DCs which present apoptotic cell-associated antigens in association with MHC II surface molecules under conditions that induce immunological tolerance to the antigen and suppress specific immunity.

In some aspects, the tolerogenic FVIII polypeptide comprises a fragment of FVIII which includes one or more known inhibitor epitopes or one or more domains, subdomains, or regions known to be targeted by inhibitor antibodies. For example, many known inhibitors act by binding to epitopes located in the 40 kDa A2 domain or 20 kDa C2 domain of Factor VIII, as described, e.g., in Fulcher et al., Proc. Natl. Acad. Sci. USA 82:7728-7732 (1985) and Scandella et al., Proc. Natl. Acad. Sci. USA 85:6152-6156 (1988). Thus, in some aspects, the tolerogenic FVIII polypeptide comprises a fragment of FVIII which comprises the A2 domain and/or the C2 domain. Without being bound by a particular theory, it is believed that exposing tolerance mediating T cells (e.g., $T_{reg}$ cells) to antigens targeted by inhibitor antibodies can inhibit or prevent the development of an immune response or the induction of a memory immune response against FVIII.

Primary cells can be vector modified directly, or they can be cultured and passaged (plated and resuspended) prior to transfection or transduction. A variety of transfection and transduction protocols are known in the art. For example, cells can be transfected by electroporation, microinjection, calcium phosphate precipitation, polybrene precipitation, or liposome fusion. Cells can be transduced by, e.g., receptor-mediated gene delivery of a viral vector, such as an adenovirus vector, an adeno-associated virus vector, a herpes simplex virus vector, a foamy virus vector, a lentivirus vector, a retrovirus vector, or the like.

In some preferred aspects, cells are transfected, cultured and/or subcultured under conditions that allow the DNA to stably incorporate into the host cell's genomic DNA (preferably with additional vector sequences capable of directing expression of the exogenous coding sequences) to produce a clonally derived strain of transfected secondary cells. Materials and methods for transfecting or transducing and/or maintaining primary or secondary vertebrate cells under conditions that favor homologous recombination and stable incorporation of exogenous DNA into the recipient cell genome are known in the art and are described, e.g., in U.S. Pat. Pub. No. 20050032215 and references cited therein. In further aspects, the exogenous nucleic acid exists episomally within the transfected primary or secondary cells. In some aspects, expression of the exogenous nucleic acid is under the control of an inducible promoter, while in other aspects the exogenous nucleic acid is constitutively expressed.

Apoptosis is induced in the primary or secondary cells using methods known in the art. Apoptosis is a process of programmed cell death, wherein the cell enters a stage characterized by the breakdown or disappearance of cellular components essential to maintenance of the normal differentiated state of the cell, while maintaining an intact, non-porous membrane. Some apoptotic cells can undergo a process of de-differentiation wherein they lose the ability to retain a differentiated state. Other signs of apoptosis include, but are not limited to, loss of membrane potential of the mitochondria, cleavage of proteins, cleavage of DNA, and protein phosphorylation and exposure of phosphatidylserine. The induction of apoptosis may be confirmed by various methods known in the art, such as DNA electrophoresis, staining with dUTP and terminal transferase (TUNEL), annexin-FITC plus propidium iodide (PI) staining, caspase activation, cleavage of target proteins, morphological changes (e.g., using light microscopy with appropriate staining or electron microscopy), or a combination thereof.

In various aspects, apoptosis can be induced by exposing the cells to an apoptosis-inducing agent, such as a corticosteroid, cyclophosphamide, methotrexate, azathioprine, cyclosporine, or staurosporine, and/or by exposing the cells to apoptosis-inducing environmental conditions, such as U.V. or gamma-irradiation, heating, cooling, serum deprivation, growth factor deprivation, acidifying, diluting, or alkalizing conditions, and/or osmotic shock. Apoptosis is preferably induced ex vivo (e.g., in vitro), but may also be induced in vivo or in situ.

In some preferred aspects, apoptosis is induced by U.V. or gamma-irradiation under conditions that induce apoptosis in the majority of cells with little or no necrosis. For example, exposure of cells to UV light (e.g., 60 mjules/cm$^2$/sec for about 1 to 10 minutes) can induce apoptosis in a variety of cell types. "Necrosis" refers to cell death resulting from sudden, irreversible trauma (e.g., by osmotic shock or exposure to chemical poison) and is characterized by marked swelling of the mitochondria and cytoplasm, followed by cell destruction and autolysis leading to the release of toxic intracellular contents which induce inflammation (Wyllie, Eur. J. Cell. Biol. 73: 189-197 (1997)). Without being limited by a particular theory, it is believed that necrotic cells are processed by a population of activated DCs which present donor cell antigens in association with MHC II molecules, leading to the induction of CD4$^+$ helper T cell immunity, rather than immune suppression and tolerance. Thus, in some preferred aspects, apoptotic cells comprise at least about 50%, or preferably at least about 75%, or more preferably at least about 85% of the cell population. In further aspects, primary and secondary necrotic cells comprise less than about 15%, or preferably less than about 10%, or more preferably less than about 5% of the total number of cells, or even more preferably less than about 1% of the total number of cells.

Transfected apoptotic cells can be administered to a subject using methods and routes of administration known in the art, including, e.g., implantation via subcutaneous, intrathecal, intravascular, intrahepatic, intrasplanchnic, intraperitoneal, or intramuscular injection. Without being limited to any particular theory, it is believed that certain apoptotic cells are selectively phagocytosed by a subpopulation of dendritic cells (DCs) capable of inducing immunological tolerance to the expressed antigen (tolerogenic DCs). In some preferred aspects, the tolerogenic DCs are CD8α$^+$ splenic DCs. While the exact mechanism by which tolerogenic DCs induce tolerance upon phagocytosis of apoptotic cells is unknown, it is believed that tolerogenic DCs can present apoptotic cell antigens on cell surface MHC II and activate antigen-specific CD4$^+$CD25$^+$ regulatory T cells, which in turn suppress CD4$^+$ effector T cell-mediated immunity. The findings reported herein surprisingly indicate that antigen presentation by tolerogenic DCs is capable of suppressing not only immune priming but also the development of anamnestic immune responses. While the mechanism by which tolerogenic DCs suppress anamnestic immune responses is also unknown, it is believed that tolerogenic DCs can present antigens directly to CD4$^+$ effector T cells and thereby suppress proliferation and/or induce deletion of the CD4$^+$ effector T cells. Tolerogenic DCs also present antigen to regulatory T cells that mediate suppression of T effector cell proliferation and activation.

In some aspects, apoptotic cells expressing a tolerogenic FVIII polypeptide are administered in combination with one or more immunosuppressive agents. For example, in some aspects, the apoptotic cells are administered in combination with an anti-inflammatory cytokine (e.g., interleukin-10 (IL-10), TGF-β, IL-4) or an agent that modulates the expression and/or activity of an inflammatory mediating cytokine 1n some aspects, the apoptotic cells are administered in combination with an antibody or ligand that blocks costimulatory signaling involved in the induction of an immune response (e.g., a blocking anti-CD40 antibody (e.g.: M2 or M3) for blocking B cell and DC activation and/or a CTLA-4 antibody, such as CTLA-4-Ig, for blocking T cell activation). In some aspects, the apoptotic cells are also transfected or transduced with a vector encoding an immunosuppressive agent, such as IL-10 or indoleamine 2,3-dioxygenase (IDO), whereas in other aspects, the apoptotic cells can be administered together with an immunosuppressive agent, such as rapamycin, cyclosporine-A, FK-506, azathioprine, cyclophosphamide, gold salts, sulfasalazine, methotrexate, D-penicillamine, hydroxychloroquine, a corticosteroid, a glucocorticoid, an inhibitor of TNF-alpha or interleukin-1, or the like.

In some aspects, methods and compositions provided herein are useful in conjunction with established means of ITI against FVIII. ITI protocols for hemophilia patients, including patients with high titer inhibitors against FVIII, are known in the art and are generally described, e.g., in Mariani et al., Thromb Haemost., 72: 155-158 (1994) and DiMichele et al., Thromb Haemost. Suppl 130 (1999). Methods provided herein can be conducted before, after, and/or concurrently with established ITI protocols and/or variations thereof. In some aspects, administering apoptotic cells expressing a tolerogenic FVIII polypeptide according to methods provided herein renders the subject more amenable to ITI. For example, in some aspects, methods provide herein increase the effectiveness of established ITI protocols (e.g., the degree and/or likelihood of successful treatment) and/or reduce associated costs or side effects. In further aspects, methods provide herein allow established ITI protocols to be beneficially modified, e.g., to decrease the frequency, duration, and/or dose of FVIII administration.

Also provided herein are pharmaceutical compositions comprising apoptotic cells as described herein together with one or more pharmaceutically acceptable excipients. The compositions can be administered by any means (e.g., injection) which produces the desired effect in the subject. In some preferred aspects, cellular compositions described herein comprise autologous cells harvested from the subject which have been expanded in culture, transfected or transduced, induced to apoptosis, and formulated in a composition suitable for administration to the subject (e.g., at the site from which the cells were harvested). Cellular compositions may be administered by subcutaneous, intraperitoneal, intramuscular, intradermal, intravenous or intralymphoid injection, or by any other suitable means.

The number of cells injected into a subject may vary depending on the size of the individual, the site of administration, and/or other factors commonly considered in determining dosages of pharmacological agents. For example, in some aspects, between about $10^3$ and $10^{11}$ cells, and more typically between about $10^5$ and $10^7$ cells, may be administered. Single or multiple (e.g., 2, 3, 4 or 5) administrations of the cells can be carried out with cell numbers and pattern being selected by the treating physician. The cells should be administered in a pharmaceutically acceptable carrier which is non-toxic to the cells and the subject, and does not modulate the necrotic and/or apoptotic state of the cells. Such carrier may be the growth medium in which the cells were grown, or any suitable buffering medium such as phosphate buffered saline.

In some aspects, formulations provided herein are in the form of a liquid solution or suspensions of cells suitable for parenteral administration. Such parenteral formulations may comprise, for example, physiological saline or phosphate buffered saline as a vehicle for intravenous infusion. Examples of useful parenteral delivery systems include, but are not limited to, ethylene-vinyl acetate copolymer particles, osmotic pumps, implantable infusion systems, and liposomes. Methods are known in the art for making such formulations and are described in, e.g., Remington's Pharmaceutical Sciences, 19th Ed., Easton, Pa., Mack Publishing Co., 1995.

Having now generally described the invention, the same will be more readily understood through reference to the following examples which are provided by way of illustration, and are not intended to be limiting of the disclosed invention, unless specified.

EXEMPLARY ASPECTS

Example 1

Materials and Methods

Animals

Studies were performed on 8-12 week old exon 16 knockout (KO) hemophilia A mice in the 129SV background strain (Bi et al., Nat Genet; 10: 119-121 (1995); Bi et al., Blood; 88:3446-3450 (1996)). Mice were housed under specific pathogen-free conditions in a University of Washington animal facility and studied in accordance with an Institutional Animal Care and Use Committee (IACUC) approved protocol. Blood was obtained by cardiac puncture or tail nick, anticoagulated with 0.1 M sodium citrate at a 9:1 (vol/vol) ratio. Plasma and serum samples were isolated immediately after blood draw and were stored at −80° C. until analyzed.

Foamy Virus Vector Constructs and hFVIII Expressing Fibroblasts

The pΔΦMscvF8IZ and control pΔΦMscvIZ vectors were generated using standard molecular cloning techniques (see e.g., Sambrook et al.) using the cDNA encoding full-length human FVIII from the PMT2-VIII vector (Pittman and Kaufman, Proc Natl Acad Sci USA; 85:2429-2433 (1988); Toole et al., Proc Natl Acad Sci USA; 83:5939-5942 (1986)) (SEQ ID NO:1) and the IRES-Zeo fragment from the MIZV vector (SEQ ID NO:2). Vector stocks were generated as previously described in Josephson et al., Hum Gene Ther; 15:87-92 (2004) and Trobridge et al., Mol Ther; 6:321-328 (2002), both of which are herein incorporated by reference. A fibroblast cell line was generated from a tail-snip of a hemophilia A mouse (Lander et al., J Natl Cancer Inst; 60:477-478 (1978)) and grown in Dulbeccos Modified Eagles Medium (DMEM) supplemented with 10% Fetal Calf Serum (FCS, Hyclone, Logan, Utah), 100 IU/ml penicillin G, 100 μg/ml streptomycin, and 1.25 μg/ml amphotericin B. Cells were transduced with foamy virus vectors and then selected in media with 1000 μg/ml zeocin (Invitrogen, Carlsbad, Calif.).

FVIII Protein Expression

FVIII protein production by transduced fibroblasts was measured in culture media with an ELISA kit per manufacturer's instructions (Matched-Pair Antibody Set for ELISA of hFVIII antigen, Affinity Biologicals, INC, Ancaster, ON, Canada). Cell lysates were prepared and Western blots were performed as previously described (Lannutti et al., Exp Hematol; 31:1268-1274 (2003)). Western blots were probed with a sheep polyclonal anti-hFVIII IgG (Affinity Biologicals, INC) at a 1:1000 dilution and a secondary donkey anti-sheep HRP (Enzyme Research, South Bend, Ind.) at a 1:2000 dilution. Intra-cellular staining of hFVIII was performed using the sheep polyclonal anti-hFVIII at a 1:100 dilution and an Alexa Fluor 488 donkey anti-sheep IgG (H+L) (Molecular Probes, Eugene, Oreg.) at a 1:100 dilution (Ye et al., Mol Ther; 10:117-126 (2004)).

Immunizations and Cell Infusions

FVIII immunized mice received 1 to 8 Intravenous (i.v.) doses of 0.2 μg of recombinant human FVIII (rhFVIII, Baxter Healthcare, Glendale, Calif.). Ovalbumin (OVA, Sigma-Aldrich, St. Louis, Mo.) immunized mice received 4 i.v. doses of 50 µg each. Fibroblasts were treated with 230 µW/cm² UV irradiation from a 300 nm source or with osmotic shock as previously described (Liu et al., J Exp Med; 196: 1091-1097 (2002), hereby incorporated by reference). Cell viability was analyzed by Annexin V-FITC and PI (propidium iodide) staining and flow cytometry per manufacturer's instructions (Annexin-VFLUOS Staining kit, Roche Applied Science, Indianapolis, Ind.). For in vivo tracking of infused fibroblasts, cells were stained with PKH (Maeda et al., J Immunol; 174: 5968-5976 (2005)) dye as directed by the manufacturer (Sigma-Aldrich) prior to UV irradiation or osmotic shock.

Cell Isolation, T Cell Proliferation, and Suppression Assays

Spleens were digested with 2 mg/ml collagenase D (Molecular Probes) for 30 min at 37° C. DCs were purified by CD11c (N418) magnetic microbeads (Miltenyi Biotech). Co-stimulatory molecules on DCs were examined by staining with anti-mouse CD11c-APC, anti-mouse CD8α-PE, anti-mouse CD80-FITC, anti-mouse CD86-FITC, and anti-mouse MHC Class II-FITC (all from eBioscience, San Diego, Calif.) and analyzing the stained cells by flow cytometry.

CD4⁺ T cells and CD90-antigen presenting cells were purified from spleens using appropriate MACS isolation kits (Miltenyi Biotech). CD4⁺CD25⁺ regulatory T cells and CD4⁺CD25⁻ effector T cells were sorted on a FACSVantageSE II machine (Becton Dickinson) after staining MACS kit purified CD4⁺ cells with an APC rat anti-mouse CD25+ antibody (eBiosciences, San Diego, Calif.). The purity of all isolated cell subsets was ≥90%. Flow cytometry cell analysis was performed on a FACS Calibur machine (Becton Dickinson), and T cell proliferation assays were carried out as previously described (Wu et al., Thromb Haemost; 85:125-133 (2001), herein incorporated by reference). In brief, 4–5×10⁵ irradiated (3000 rad) CD90 depleted splenocytes were co-cultured in wells of 96 well plates with 1×10⁵ splenic CD4⁺ T cells from pools of 3-5 mice in 200 µl/well RPMI 1640 complete media (Morita et al., J Clin Invest; 107:1275-1284 (2001)) supplemented with increasing concentrations of rhFVIII or OVA. After 72 hours of co-culture, 1 µCi 3H-thymidine was added to the media and 18 hours later cells were harvested and incorporation of the radiolabel was determined on a β-scintillation counter. All data points were generated in triplicate and the results are expressed as a stimulation index (SI), corresponding to the ratio of the average cpm of cultures in the presence of the antigen to the average basal proliferation of the same cells with medium alone (Evans and Morgan, Proc Natl Acad Sci USA; 95:5734-5739 (1998)).

For suppression assays, 5×10⁴ CD4⁺CD25⁻ splenic T cells from rhFVIII or OVA immunized mice were co-cultured with varying numbers of CD4⁺ CD25⁺ T cells from apoptotic fibroblast treated mice in the presence of 2.5×10⁵ irradiated (2500 rad) CD90 depleted splenocytes. Media (RPMI complete media) was supplemented with either 4 nM rhFVIII or 500 µg/ml OVA to stimulate proliferation of splenic Teffs. After 72 hrs, 1 µCi 3H thymidine was added to the media and cells were cultured for an additional 18 hours prior to determining incorporation of the radiolabel by proliferating cells.

Detection of Total Anti-hFVIII and Anti-OVA IgG

Anti-FVIII and anti-OVA IgG titers were determined by ELISA as previously described (Reipert et al., Thromb Haemost; 84:826-832 (2000); Yang et al., Nat Biotechnol; 26:326-334 (2008), both of which are herein incorporated by reference). Briefly, the solid phase of MaxiSorp™ flat-bottom 96 well plates (Nalge Nunc International, Rochester, N.Y.) were coated with rhFVIII (0.2 µg in 200 µl/well) or OVA (0.4 µg in 200 µl/well) and then incubated with serial dilutions of mouse serum. The bound anti-FVIII or anti-OVA antibodies were detected by probing with an alkaline phosphatase (AP) conjugated goat antimouse IgG (Southern Biotech, Birmingham, Ala.) and developed using phosphatase substrate (Sigma-Aldrich). An absorbance value above twice the mean obtained using pooled serum from naive mice was regarded as positive and the titer was reported as the highest positive dilution detected.

Bethesda Assay

The FVIII inhibitor titer was determined by Bethesda assay using the protocol of Thompson and Counts, J Lab Clin Med; 88:922-929 (1976) (herein incorporated by reference) with minor modification. In brief, equal volumes of pooled normal human citrated plasma (DiaPharma, West Chester, Ohio) and serial dilutions of murine plasma samples (in 0.05 M imidazole buffer) were incubated together at 37° C. for 2 hours. FVIII activity was determined as described using a one-stage, kaolin-activated assay in a semi-automated system (CoaScreener; American Labour, Raleigh, N.C.). The dilution of test plasma giving a residual FVIII activity of 50% was defined as one Bethesda unit FVIII inhibitor activity per milliliter.

Cytokine Profiling of T Cells by ELISA

Splenic CD4⁺ T cells (1×10⁶ cells/well in 24 well plates) were stimulated with 3 nM FVIII in the presence of 4-5×10⁶ irradiated (3000 rad) CD90 depleted splenocytes in RPMI1640 complete medium. ELISA (eBiosciences) assays on supernatant samples were used to measure IL-4 and IFN-γ levels at 48 hours and IL-10 levels at 72 hours. The bioactive form of TGF-β1 was measured at 72 hours with the TGF-β1 Emax ImmunoAssay System (Promega, Madison, Wis.).

Adoptive Transfer Studies

CD4⁺ cells were purified from the spleens of donor mice at 72-96 hours after the second of two weekly infusions of fibroblasts. Naive secondary recipients were infused with 1×10⁶ CD4⁺ splenocytes and immunizations with 4 weekly doses of rhFVIII were started 24 hours later.

Statistical Analysis

Data is presented as mean±SE. The significance of the differences for each immunologic experiment was evaluated using the Student's t test. A regression model was used to evaluate effects of AC infusion on FVIII inhibitor antibody titers in pre-immunized mice. Post AC infusion inhibitor titers were regressed on pre AC infusion titers and treatment group was included as a categorical covariate. Overall treatment effects were evaluated by testing hypotheses comparing differences among groups for predicted post-infusion titer levels assuming the same pre-infusion titer level.

Example 2

Establishment of a FVIII Transgene-expressing Fibroblast Cell Line

A fibroblast cell line was generated from a tail snip of a FVIII KO mouse (Lander et al., J Natl Cancer Inst; 60:477-478 (1978)). Fibroblasts were transduced with a bicistronic foamy virus vector expressing full length human FVIII (ΔΦMscvF8IZ) or a control vector (ΔΦMscvIZ), and the cells were placed under zeocin drug selection. FIG. 1A shows foamy virus vectors ΔΦMIZ and ΔΦMF8IZ that contain the murine stem cell virus promoter (M), an internal ribosomal entry site (I) and the zeocin resistance gene (Z). CHO-K1 cells represent a negative control; 10A1 cell line are CHO-K1 cells modified to express full-length human FVIII61; Fibro/IZ cells are a fibroblast cell line from 129SV FVIII KO mice transduced with the ΔΦMIZ vector; Fibro/F8IZ cells are the same fibroblast cell transduced with the ΔΦMF8IZ vector. The upper band in both the 10A1 and Fibro/F8IZ cells are uncleaved full-length FVIII and the smaller bands represent different degrees of proteolysis.

Both vector modified cell lines (Fibro/F8IZ and Fibro/IZ) were determined to be polyclonal by Southern blotting. FVIII protein expression in the Fibro/F8IZ cells was confirmed by Western blotting (FIG. 1B) and intracellular immunofluorescent antibody staining (FIG. 1C). Intracellular FVIII antigen levels were determined by ELISA; antigen and activity levels in cell culture media were also measured (Table 1). FIGS. 1A-1C show human FVIII transgene expression in a fibroblast cell line generated from 129SV exon 16 FVIII knockout mouse.

TABLE 1

Quantitation of FVIII in Fibroblast Cell Lysates and Supernatants

| Vector | FVIII antigen (ng/ml) | | FVIII activity (mU/mL) Supernatants |
|---|---|---|---|
| | Cell lysates | Supernatants | |
| F8IZ | 4.6 ± 2.1 | 2.1 ± 0.5 | 62.3 ± 5.3 |
| F309s/226aa/N6IZ | 23.6 ± 4.5 | 13.8 ± 2.0 | 190.3 ± 10.0 |

Table 1 shows FVIII expression by fibroblasts expressing either the full-length hFVIII transgene (F8IZ) or a bioengineered transgene lacking most of the B-domain (F309s/226aa/N6IZ). Compared to Fibro/F8IZ cells, there were higher levels of FVIII antigen in Fibro/F309s/226aa/N61Z cells, and higher FVIII antigen and activity levels in the supernatants of Fibro/F309s/226aa/N61Z cell cultures. FVIII protein production by transduced fibroblasts was measured in culture media with an ELISA kit per manufacturer's instructions (Matched-Pair Antibody Set for ELISA of hFVIII antigen, Affinity Biologicals, INC, Ancaster, ON, Canada). FVIII activity was measured by the COAMATIC chromogenic assay (Chromogenix, Lexington Mass.) on a BCS XP machine (Siemens Healthcare, Munich, Germany) according to the manufacturers' instructions; N=3 per group.

Example 3

Apoptotic Fibroblasts are Selectively Captured by CD8α+ Splenic DCs

Figure 2:
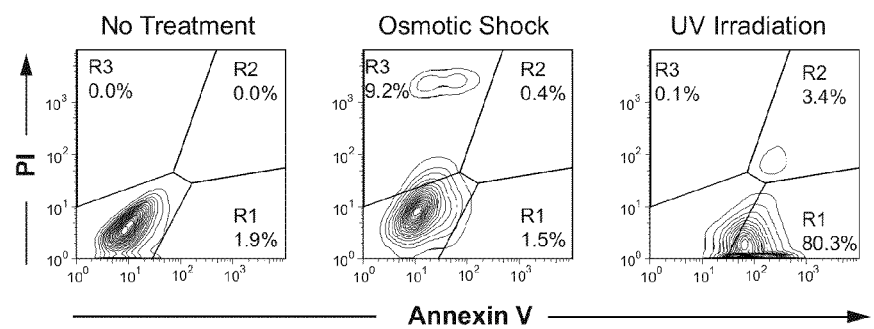
FIG. 2A is an Annexin V and PI staining of Fibro/F8IZ cells in culture and after treatment with osmotic shock or UV irradiation compared to no treatment cells. R1 represents early apoptotic cells, R2 represents late apoptotic cells and early necrotic cells, and R3 represents late necrotic cells.
FIG. 2B is a graph of the uptake of dying cells by splenic DCs using flow cytometry. Splenic DC phagocytosis of PKH26 labeled fibroblasts were administered intravenously into mice following treatment with either osmotic shock or UV irradiation. Internalization of apoptotic cells by splenic DCs was analyzed by flow cytometry at 42 hours.
FIG. 2C is a graph of expression of CD80, CD86, and MHC Class II on splenic CD11c$^+$ and CD11c$^+$CD8α$^+$DCs at 42 hours after i.v. injection of UV irradiated 1×10$^7$ Fibro/F8IZ cells. Results are shown as mean fluorescence intensity (MFI) determined by flow cytometry after antibody staining.
Figure 2:
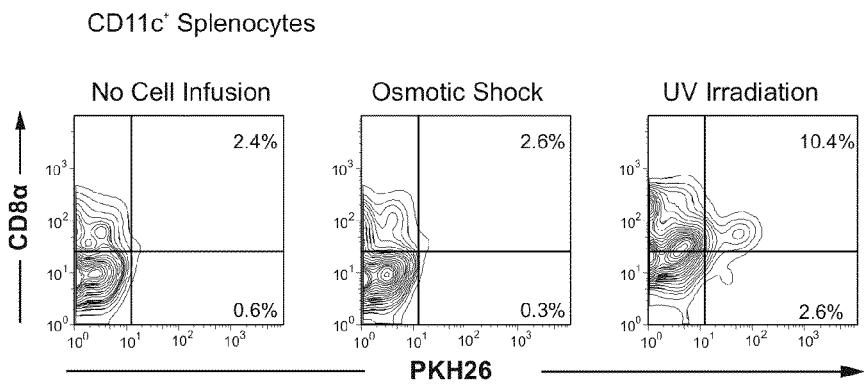
Figure 2:
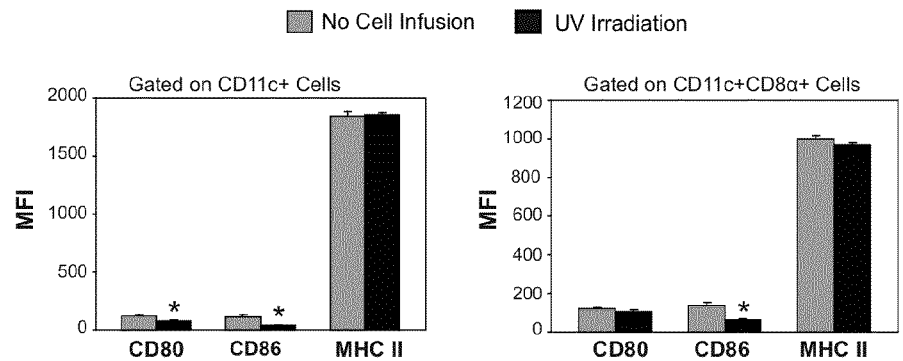

Osmotic shock has been used to generate apoptotic antigen loaded splenocytes capable of inducing tolerance (Liu et al., J Exp Med; 196: 1091-1097 (2002)). However, the same treatment of the fibroblast cell lines produced more necrosis than apoptosis. In contrast, UV irradiation reliably generated apoptosis (>50%) with little necrosis in cells evaluated at 3 hours post treatment (FIG. 2A). FIG. 2A shows Annexin V and PI staining of Fibro/F8IZ cells in culture and after treatment with osmotic shock or UV irradiation. R1 represents early apoptotic cells, R2 represents late apoptotic cells and early necrotic cells, and R3 represents late necrotic cells. Furthermore, PI and trypan blue staining of fibroblasts 24 hours post UV irradiation confirmed that treated cells were not viable (data not shown).

Splenic DC phagocytosis of PKH26 labeled fibroblasts administered intravenously were tracked following treatment with either osmotic shock or UV irradiation. After osmotic shock or UV irradiation $1 \times 10^7$ PKH26-labeled Fibro/F8IZ cells were injected intravenously into FVIII KO mice. Internalization of apoptotic cells by splenic DCs was analyzed by flow cytometry at 42 hours (FIG. 2B). CD8α expression and uptake of the PKH26 label was quantitated on CD11c splenocytes. Data are representative of two independent experiments. At 42 hours post infusion DC phagocytosis of labeled cells was only seen in mice infused with UV irradiated fibroblasts and the majority of DCs processing these cells expressed intermediate levels of CD8α. This is consistent with previous reports of in vivo processing of apoptotic splenocytes by tolerogenic DCs (Iyoda et al., J Exp Med; 195: 1289-1302 (2002); Morelli et al., Blood; 101:611-620 (2003); Wang et al., Am J Transplant; 6:1297-1311 (2006)).

Furthermore, infusion of apoptotic fibroblasts down-regulated expression of the costimulatory molecules CD80 and CD86 on splenic DCs (FIG. 2C). FIG. 2C shows expression of CD80, CD86, and MHC Class II on splenic CD11c and CD11c+ CD8α DCs at 42 hours after i.v. injection of UV irradiated $1 \times 10^7$ Fibro/F8IZ cells. Results are shown as mean fluorescence intensity (MFI) determined by flow cytometry after antibody staining.

Example 4

Suppression of FVIII Inhibitor Formation in Naive Hemophilic Mice

Figure 3:
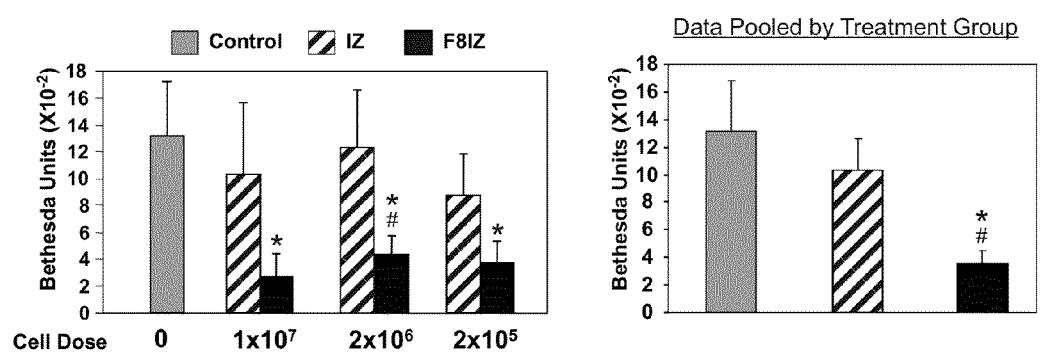
FIG. 3A is a set of graphs showing the immune response to subsequent FVIII immunization in naive hemophilic mice infused with vector modified apoptotic fibroblasts.
FIG. 3B is a set of graphs showing immune response after re-challenge with FVIII.
Figure 3:
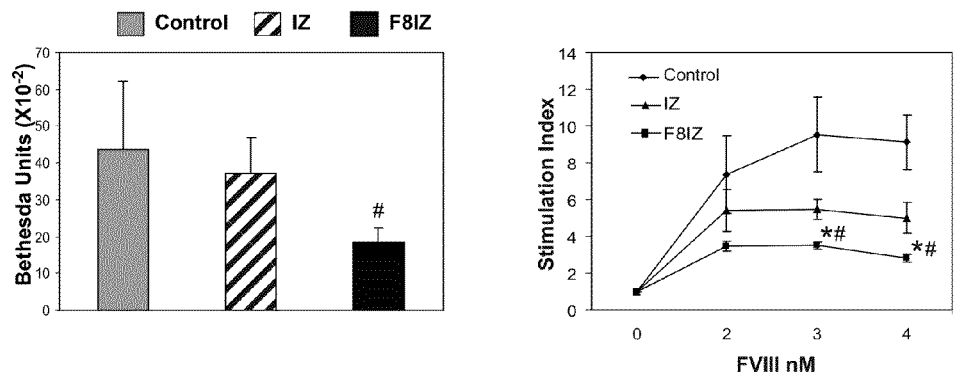

Hemophilic mice were given 2 weekly i.v. infusions of apoptotic fibroblasts at 3 different doses ($1 \times 10^7$, $2 \times 10^6$, and $2 \times 10^5$ cells per mouse) prior to immunization with 4 weekly i.v. infusions of rhFVIII. Mice treated with all 3 doses of apoptotic Fibro/F8IZ cells developed 3 to 5-fold lower mean Bethesda titers than no cell treatment controls following immunization (FIG. 3A, p<0.02 for all 3 cell cohorts). Inhibitor titers were reduced in hemophilic mice that were immunized with rhFVIII after receiving two weekly infusions of UV-irradiated Fibro/F8IZ cells. The effect was similar across a dose range of $2 \times 10^5$-$1 \times 10^7$ cells per infusion (left panel of FIG. 3A). FIG. 3A (right panel) represents data grouped by the type of ACs delivered. Control animals received no cells (* p<0.05 comparing Fibro/F8IZ to control, # p<0.05 comparing Fibro/F8IZ to Fibro/IZ. All groups N=4-5 per dose group).

Furthermore, mice that received $2 \times 10^6$ Fibro/F8IZ cells developed 3-fold lower titers than mice infused with an equivalent number of Fibro/IZ cells (p=0.04). At both the $1 \times 10^7$ and $2 \times 10^5$ cell doses, there was also a trend for lower Bethesda titers in the Fibro/F8IZ cell treated mice compared to mice treated with the same number of Fibro/IZ cells. Results grouped by type of apoptotic cells delivered (FIG. 3A, right panel) showed statistically lower Bethesda titers in Fibro/F8IZ recipients compared to both no cell treatment controls (5-fold lower, p<0.02) and Fibro/IZ treated mice (4-fold lower, p<0.02). In additional experiments, infusion of ≤$10^4$ UV irradiated Fibro/F8IZ cells produced less suppression of the immune response to subsequent rhFVIII immunization.

FIG. 3B shows mice treated at the $1 \times 10^7$ apoptotic cell dose (Fibro/F8IZ or Fibro/IZ) and no cell treatment controls were re-challenged with 4 additional weekly doses of rhFVIII 120 days after completion of the first immunization course. Mice that received Fibro/F8IZ apoptotic cells still showed lower mean titers and in vitro T cell responses to rhFVIII antigen stimulation than those treated with Fibro/IZ apoptotic cells or no cell treatment controls (FIG. 3B). However, the Bethesda titers in all 3 groups increased significantly after re-challenge indicating that the suppression of inhibitor formation from the initial dosing of apoptotic cells was overcome by the inhibitor response to the additional 4 doses of antigen. Bethesda titers (left panel) and T cell stimulation assays (right panel) with pooled splenic CD4+ T cells (4-5 mice per group) are shown in FIG. 3B. Stimulation Index (SI) data are presented as the mean±SE of assays run in triplicate for each concentration of FVIII (* p<0.05 comparing Fibro/F8IZ to control, # p<0.05 comparing Fibro/F8IZ to Fibro/IZ).

Figure 9:
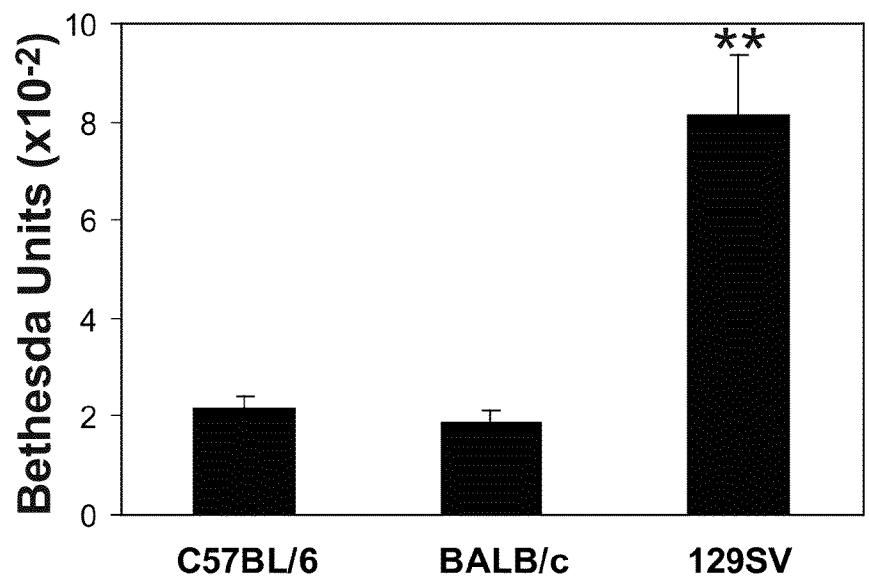
FIG. 9 is a graph showing inhibitor titers from exon 16 KO mice in the 129SV, C57BL/6 and BALB/c background strains after challenge with four weekly i.v. infusions of rhFVIII.

FIG. 9 shows inhibitor titers from exon 16 KO mice in the 129SV, C57BL/6 and BALB/c background strains after challenge with four weekly i.v. infusions of rhFVIII. 129SV strain hemophilic mice generate higher inhibitor titers than C57BL/6 and BALB/c mice in response to immunization with rhFVIII. Data shown are inhibitor titers from exon 16 KO mice in the 129SV, C57BL/6 and BALB/c background strains after challenge with four weekly i.v. infusions of rhFVIII (** p<0.01 for 129SV (N=32) vs. C57BL/6 (N=13) and for 129SV vs. BALB/c (N=20)).

Example 5

Antigen Specificity of the Immune Suppression with Fibro/F8IZ Apoptotic Cells

Figure 11:
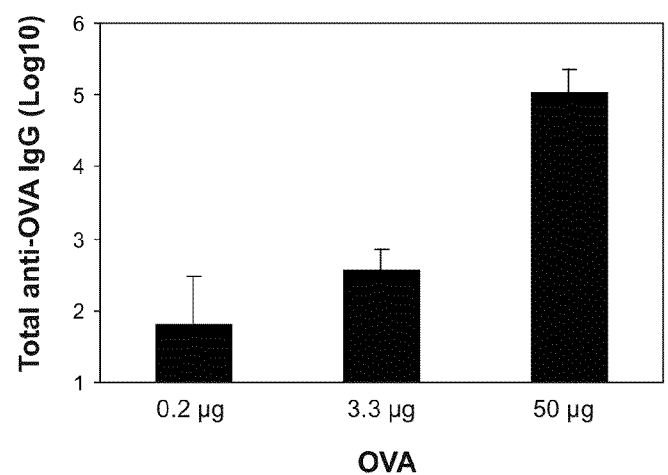
FIG. 11A is a graph showing dose response to immunization with OVA antigen in hemophilic mice. Mice were given four weekly doses of 0.2, 3.3, or 50 μg OVA by i.v. infusions and anti-OVA antibody titers were determined one week after the last infusion of antigen.
FIG. 11B is a graph showing dose response to immunization with OVA antigen in hemophilic mice. Mice were given four weekly doses of 0.2, 3.3, or 50 μg OVA by i.v. infusions and T cell assays were performed one week after the last infusion of antigen.
Figure 11:
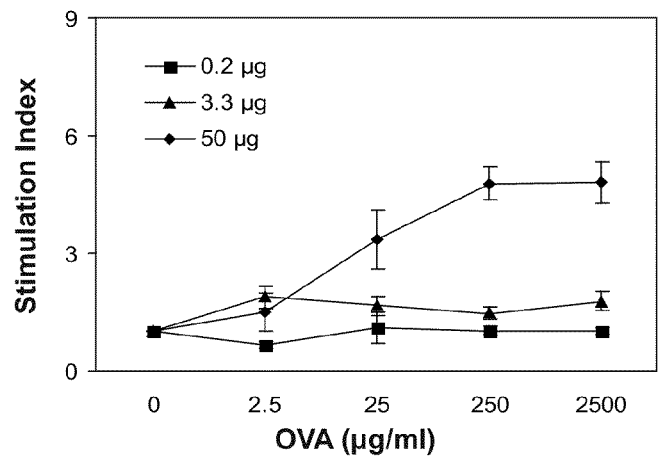

To determine if the immunosuppressive properties of apoptotic Fibro/F8IZ cells could also diminish the immune response to an unrelated antigen, OVA, hemophilic mice were given 2 infusions of 1×10$^7$ apoptotic cells (Fibro/F8IZ or Fibro/IZ), or no cells, prior to immunization with OVA antigen or rhFVIII. A dose of 50 μg of OVA antigen was used because it produces a measurable antibody and T cell response of similar magnitude to what is generated by 4 weekly doses of 0.2 μg of rhFVIII (FIG. 11). FIG. 11 shows a dose response to immunization with OVA antigen in hemophilic mice. Mice were given four weekly doses of 0.2, 3.3, or 50 μg OVA by i.v. infusions and anti-OVA antibody titers (FIG. 11A) and T cell assays (FIG. 11B) were determined one week after the last infusion of antigen.

Figure 4:
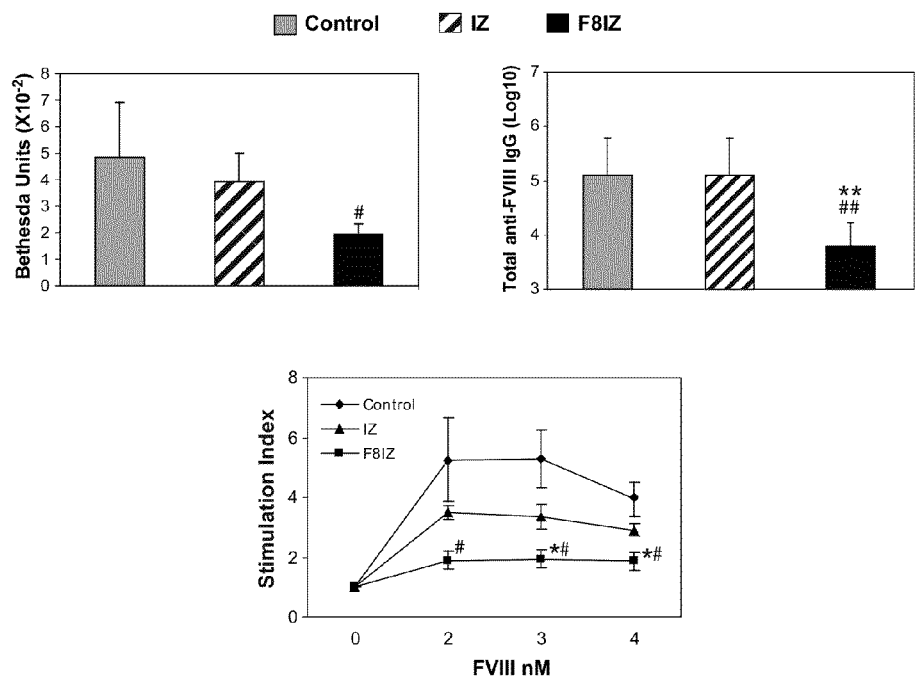
FIG. 4A shows antigen specific suppression of the immune response to rhFVIII by apoptotic fibroblasts expressing a FVIII transgene. Naive hemophilic mice were given two weekly doses of UV irradiated fibroblasts before challenge with four weekly doses of rhFVIII or OVA. Bethesda titers (upper left), total anti-FVIII IgG titers (upper right), and T cell responses to rhFVIII (lower panel) in control and AC (Fibro/IZ and Fibro/F8IZ) treated mice are shown.
FIG. 4B shows total IgG anti-OVA antibody titers (left panel) or T cell responses to OVA (right panel) in apoptotic cell treated mice compared to controls.
Figure 4:
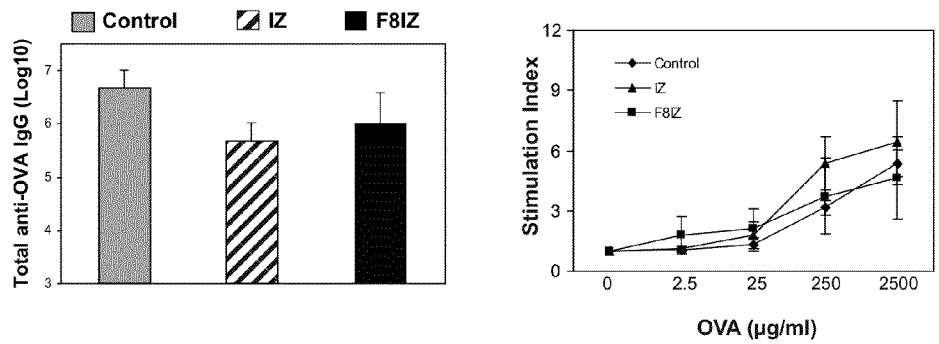

Mice that received Fibro/F8IZ cells produced lower Bethesda titers, total anti-FVIII IgG titers, and in vitro T cell responses after immunization with rhFVIII than either Fibro/IZ treated animals or no cell treatment controls (FIG. 4A). FIG. 4A shows antigen specific suppression of the immune response to rhFVIII by apoptotic fibroblasts expressing a FVIII transgene. Naive hemophilic mice were given two weekly doses of UV irradiated fibroblasts before challenge with four weekly doses of rhFVIII or OVA. Bethesda titers (upper left panel of FIG. 4A), total anti-FVIII IgG titers (upper right panel of FIG. 4A), and T cell responses to rhFVIII (lower panel of FIG. 4A) in control and AC (Fibro/IZ and Fibro/F8IZ) treated mice are shown (* p<0.05 for Fibro/F8IZ compared to control, # p<0.05 for Fibro/F8IZ compared to Fibro/IZ, ** p<0.01 for Fibro/F8IZ compared to control, ## p≤0.01 for Fibro/F8IZ compared to Fibro/IZ, N=5-6 mice per treatment group).

In contrast, infusion of apoptotic Fibro/F8IZ or Fibro/IZ cells had no effect on the T cell response to immunization with OVA, though both groups of apoptotic cell recipients did show a trend for developing lower anti-OVA IgG titers (FIG. 4B; 9.0% drop in mean log$_{10}$ titer for FibroF8IZ vs. control, p=0.37; 14.2% drop in mean log$_{10}$ titer for Fibro/IZ vs. control, p=0.1). FIG. 4B shows no significant differences in total IgG anti-OVA antibody titers or T cell responses to OVA were seen in apoptotic cell treated mice compared to control (N=3 mice per group; data are representative of three independent experiments). These data demonstrate that the marked immune suppression induced with Fibro/F8IZ apoptotic cells is limited to responses against FVIII antigen. They also suggest a minor generalized immunosuppressive effect from apoptotic cell infusions.

Example 6

Suppression of Inhibitor Formation in Pre-immunized Hemophilic Mice

We also investigated whether infusion of Fibro/F8IZ apoptotic cells could be used to suppress a robust pre-formed immune response against FVIII. Baseline pre-treatment Bethesda titers were measured in the peripheral blood of hemophilic mice 1 week following completing immunization with 4 weekly doses of rhFVIII. The immunized mice were then either given no additional treatments or 2-6 weekly infusions of 1×10$^7$ apoptotic cells (Fibro/F8IZ or Fibro/IZ). Post treatment Bethesda titers were measured in peripheral blood 1 week after the last infusion of apoptotic cells in both experiments (FIGS. 5A and 5B) and T cell responses to rhFVIII stimulation were determined at the same time in the second experiment (FIG. 5B).

FIGS. 5A-5C show suppression of inhibitor formation in pre-immunized hemophilic mice. Two weeks after completing immunization with four weekly doses of rhFVIII mice were given 2 to 6 weekly infusions of UV irradiated Fibro/IZ or Fibro/F8IZ cells. Bethesda titers were measured one week after the last infusion of cells. FIG. 5A shows Bethesda titers in mice treated with 2-4 weekly infusions of apoptotic cells. FIG. 5B shows Bethesda titers and T cell stimulation assays, on CD4+ splenocytes, in mice treated with 4-6 weekly infusions of apoptotic cells, * p≤0.05 Fibro/F8IZ×6 vs. control, # p<0.05 Fibro/F8IZ×6 vs. Fibro/IZ×6 and F8IZ×4 vs. IZ×4, $ p<0.05 F8IZ×4 vs. control N=3-5 mice per group. FIG. 5C shows effects of treatment of pre-immunized mice with 6 weekly infusions of apoptotic Fibro/F8IZ cells and Bethesda titers were measured 1, 3, and 5 weeks after the last dose of cells.

Because individual inhibitor responses to rhFVIII immunization in hemophilic mice are quite variable, a comparison of pre- and post treatment titers for each animal was performed (FIGS. 5A and 5B). As graphed, points located above the solid line at 45° represent animals with higher post treatment titers and points below the line represent animals with lower post treatment titers. The inhibitor response had not peaked by 1 week after the last rhFVIII infusion as all mice in the no cell treatment control groups exhibited increases in Bethesda titers over time. In contrast, mice that received multiple infusions of apoptotic Fibro/F8IZ cells had significantly lower post treatment Bethesda titers. The impact of apoptotic cell infusions was quantitated from a regression analysis of data in each treatment group. The predicted post treatment Bethesda titer for each cohort was calculated based on a pre-immunized titer equal to the median value for all mice in each experiment (Tables 2 and 3).

TABLE 2

Treatment Effects of 2-4 Infusions of Apoptotic Cells in Pre-immunized Mice - Experiment 1

| Treatment Group | Estimated Slope | Predicted Post-Trt Titer for Pre Titer = 400 | Trt Effect: Difference from Control | % Reduction Relative to Control | p-value |
|---|---|---|---|---|---|
| Control | 1.02 | 957.5 | | | |
| Fibro/IZx2 | 0.53 | 664.0 | −293.6 | 30.7% | 0.003 |
| Fibro/IZx4 | 1.76 | 504.0 | −453.5 | 47.4% | <0.001 |
| Fibro/F8IZx2 | 1.08 | 442.6 | −515.0 | 53.8% | <0.001 |
| Fibro/F8IZx4 | 0.04 | 232.0 | −725.6 | 75.8% | <0.001 |

Results for the Control group show that titer levels were expected to rise if mice were left untreated (immunized but not given any AC therapy). The median pre-treatment titer for all mice in the experiment was 400BU. A mouse in the Control group with an initial titer level of 400BU was expected to develop a titer of 548+1.02×400=957.5 BU (intercept+slope× initial Bethesda titer) by the end of the 'treatment' period. Mice in all treatment groups showed significant reductions in post infusion titers compared to the control group.

TABLE 3

Treatment Effects of 4-6 Infusions Apoptotic Cells in Pre-immunized Mice - Experiment 2

| Treatment Group | Estimated Slope | Predicted Post-Trt Titer for Pre Titer = 650 | Trt Effect: Difference from Control | % Reduction Relative to Control | p-value |
|---|---|---|---|---|---|
| Control | 1.20 | 1112.4 | | | |
| Fibro/IZx4 | 1.15 | 1033.4 | −79.0 | 7.1% | 0.74 |
| Fibro/IZx6 | 0.61 | 671.8 | −440.6 | 39.6% | 0.1 |
| Fibro/F8IZx4 | 0.60 | 420.5 | −691.9 | 62.2% | 0.01 |
| Fibro/F8IZx6 | 0.12 | 187.9 | −924.5 | 83.1% | 0.003 |

The median pre-treatment titer for all mice in this experiment was 650BU. A mouse in the Control group with an initial titer level of 650BU was expected to develop a titer of 1112.4 BU by the end of the 'treatment' period. Mice in the Fibro/F8IZ×4 and Fibro/F8IZ×6 groups showed significant reductions in post infusion titers compared to control group.

In both experiments the actual post-treatment Bethesda titers in Fibro/F8IZ treated mice were significantly lower (53.8% to 83.1%) than predicted values and there was evidence of a dose effect for the number of infusions of ACs. In contrast, post-treatment titers in Fibro/IZ treated mice were 7.1% to 47.4% less than predicted. Furthermore, there was near complete suppression of proliferation of CD4+ splenocytes in response to rhFVIII stimulation in cells from mice that received treatment with 4 or 6 weekly infusions of Fibro/F8IZ apoptotic fibroblasts (FIG. 5B). Treatment with Fibro/IZ apoptotic cells resulted in a 2-3 fold fall in the proliferation rate of CD4+ splenocytes.

An additional cohort of pre-immunized mice received 6 weekly infusions of Fibro/F8IZ ACs and had serial inhibitor titers measured for 5 weeks after receiving the last dose of cells. As shown in FIG. 5C, at 1 week post-treatment with Fibro/F8IZ ACs the mean inhibitor titer dropped by 80% (from 546.2±153.1 BUs to 110±19.0 BUs) and then remained stable at 3 weeks (92.8±6.8 BUs) and 5 weeks (96.8±11.4 BUs) post treatment. Thus, multiple infusions of hFVIII transgene modified apoptotic fibroblasts markedly suppressed both inhibitor production and T cell responses in pre-immunized animals, and the reductions in inhibitor titers remained stable for at least 5 weeks after the last AC infusion.

Figure 5:
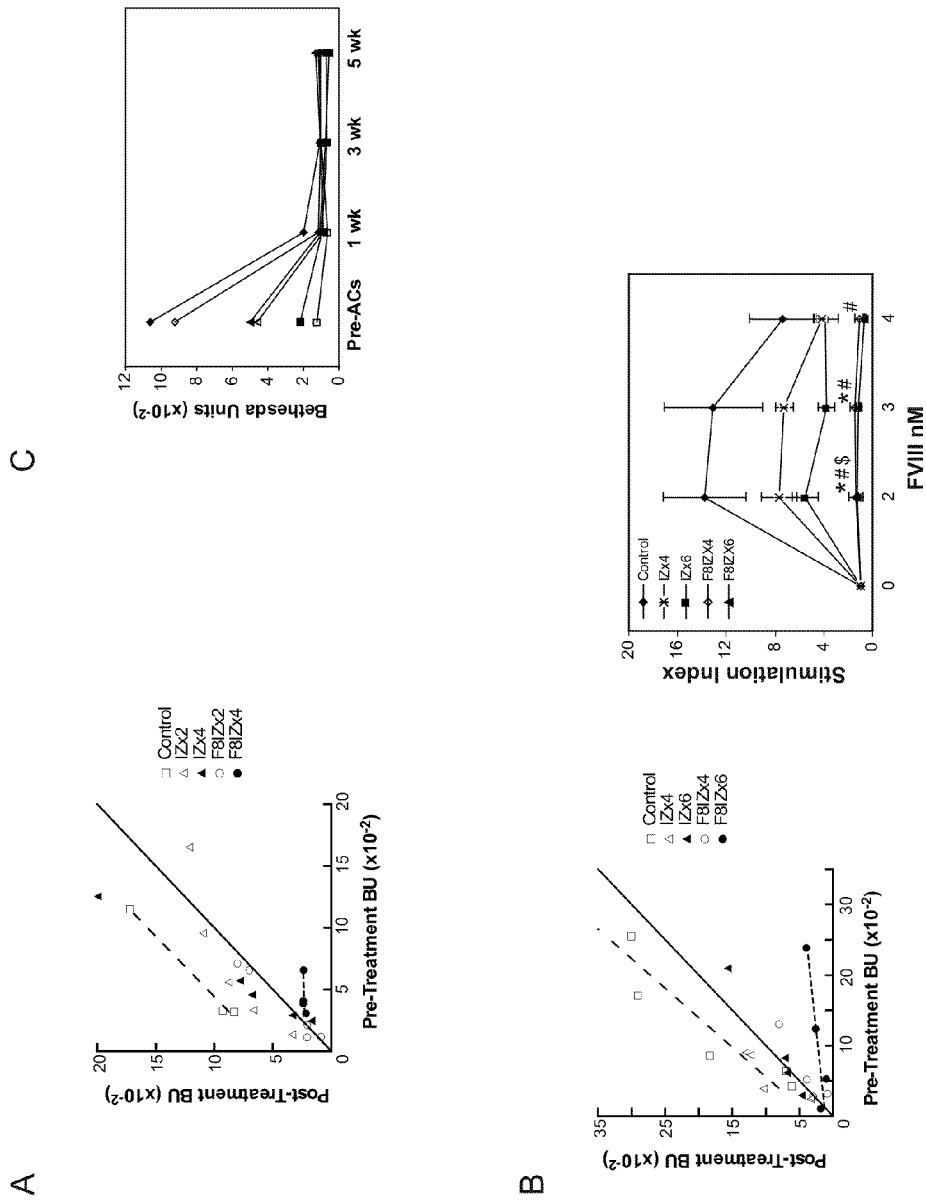
FIG. 5A shows Bethesda titers in pre-immunized hemophilic mice treated with 2-4 weekly infusions of apoptotic cells.
FIG. 5B shows Bethesda titers and T cell stimulation assays on CD4$^+$ splenocytes, in mice treated with 4-6 weekly infusions of apoptotic cells.
FIG. 5C is a graph showing Bethesda titers measurements in pre-immunized mice that were treated with 6 weekly infusions of apoptotic Fibro/F8IZ cells and were measured 1, 3, and 5 weeks after the last dose of cells.
Figure 6:
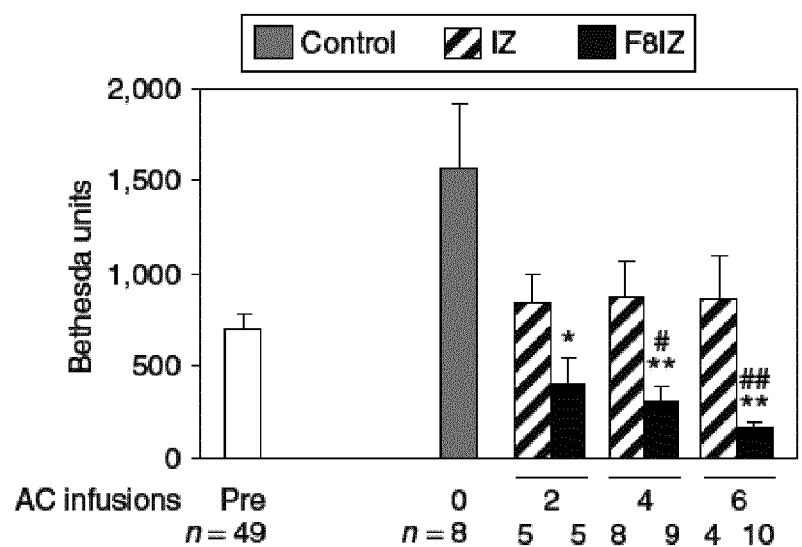
FIG. 6 contains the same data as presented in FIGS. 5A-5C but in a different form.

FIG. 6 shows the same inhibitor titer data from the 3 separate experiments presented in FIG. 5. Here, all the data is grouped by the number of infusions of UV irradiated Fibro/IZ and Fibro/F8IZ cells infused. It demonstrates suppression of inhibitor formation in pre-immunized hemophilic mice by FVIII expressing apoptotic cells with a clear dose response for the number of infusions of Fibro/F8IZ cells given(* $P<0.05$ Fibro/F8IZ vs. control, ** $P<0.01$ Fibro/F8IZ vs. control, # $P<0.05$ Fibro/F8IZ vs. Fibro/IZ, ## $P<0.01$ Fibro/F8IZ vs. Fibro/IZ). A total of 49 mice were treated (N=4-10 per post-treatment group).

Example 7

Cytokine Production of CD4+ T Cells After Transfusion of Apoptotic Cells

Figure 7:
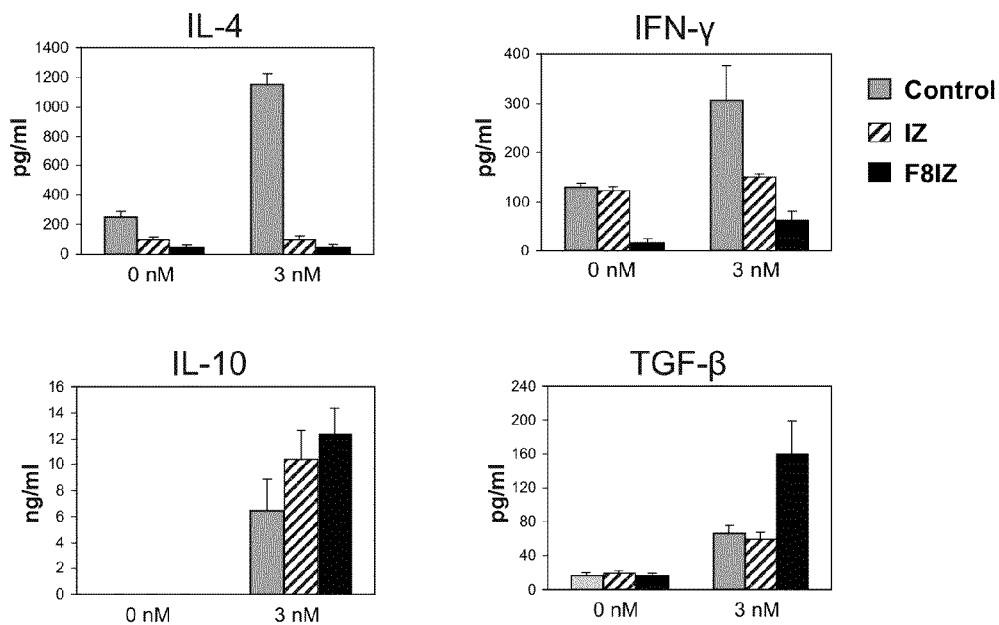
FIG. 7A is a set of graphs that show cytokine production by in vitro stimulated CD4$^+$ splenocytes from apoptotic cell treated hemophilic mice.
FIG. 7B is a graph of the relative production of cytokines by CD4$^+$ cells from Fibro/F8IZ and Fibro/IZ treated mice compared to no cell controls.
Figure 7:
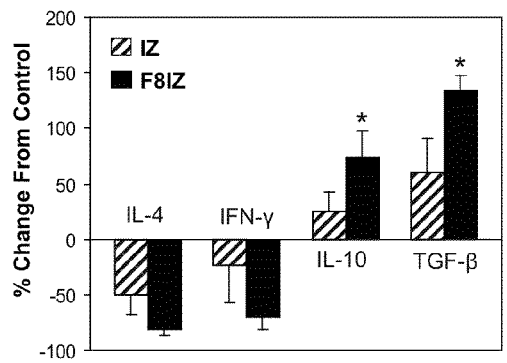

Cytokine analysis of supernatants from the T cell stimulation assays (FIG. 3B and FIG. 4A) was performed. As shown in FIGS. 7A and 7B, T cells from animals treated with apoptotic fibroblasts (either Fibro/F8IZ or Fibro/IZ) produced lower amounts of the inflammatory cytokines IL-4 and INF-γ than no cell treatment controls, though the degree of suppression was greatest in T cells from Fibro/F8IZ treated mice. In contrast, expression of the anti-inflammatory cytokines IL-10 and TGF-β was higher in T cells from apoptotic cell treated mice compared to no treatment controls, and again the effect was more pronounced in T cells from Fibro/F8IZ treated animals. These data demonstrate apoptotic cell induced suppression of both the Th1 and Th2 responses to FVIII and the induction of a CD4+ T cell mediated anti-inflammatory response. A more pronounced effect was induced by apoptotic cells carrying FVIII antigen.

In FIGS. 7A and 7B, naive hemophilic mice were treated with two infusions of Fibro/F8IZ or Fibro/IZ apoptotic cells and then challenged with four weekly doses of rhFVIII. Pooled splenic CD4+ T cells from 3-5 mice in each group were incubated with 3 nmol/l rhFVIII for 3 days. Levels of IL-4, IFN-γ, IL-10 and TGF-β were measured from culture media by ELISA. Results are shown as the mean±SE of cytokine levels determined on triplicate assays in a representative experiment (FIG. 7A). Differences in the production of cytokines by CD4+ cells from Fibro/F8IZ and Fibro/IZ treated mice compared to no cell controls are shown in FIG. 7B. Data are pooled from five independent experiments (* p<0.05 for Fibro/F8IZ vs. Fibro/IZ, **p<0.01 for Fibro/F8IZ vs. control, #P<0.05 for Fibro/F8IZ vs. Fibro/IZ).

Example 8

Immune Suppression Induced by FVIII Expressing Apoptotic Cells is Transferable with Splenic CD4+ T Cells To determine if the immune suppression induced by apoptotic cells is an active process mediated by CD4+ T cells, adoptive transfer studies were performed using CD4+ splenocytes harvested from Fibro/F8IZ and Fibro/IZ treated mice at 90 hours post completion of a course of 2 or 4 weekly infusions of $1\times10^7$ apoptotic fibroblasts. Secondary recipients were started on an immunization course of 4 weekly doses of rhFVIII one day after adoptive transfer of $1\times10^6$ splenic CD4+ T cells. Secondary recipients of CD4+ cells from primary mice treated with 2 doses of Fibro/F8IZ cells showed 45% lower inhibitor titers than secondary recipients of CD4+ cells from primary mice treated with 2 doses of Fibro/IZ cells and 50% lower titers than mice given no cells prior to rhFVIII immunization (FIG. 8A). One week following the last immunization dose Bethesda titers were measured (N=8-9 mice per group in the 2 cell treatment study, FIG. 8A).

The suppression was even more pronounced in secondary mice given splenic CD4+ T cells from primary mice treated with 4 doses of Fibro/F8IZ cells (FIG. 8B). They generated 67% lower inhibitor titers than secondary recipients of CD4+ cells from primary mice treated 4 doses of Fibro/IZ cells and 63% lower titers than mice given no cells prior to rhFVIII immunization (left panel of FIG. 8B). Furthermore, FVIII induced T cell proliferation was markedly suppressed in the secondary mice given CD4+ splenic T cells from primary mice treated with Fibro/F8IZ cells (right panel of FIG. 8B). (N=5-6 mice per group in the 4 cell treatment study, * p<0.05 for Fibro/F8IZ vs. control, # p<0.05 for Fibro/F8IZ vs. Fibro/IZ, ** p<0.01 for Fibro/F8IZ vs. control and ## p<0.01 for Fibro/F8IZ vs. Fibro/IZ).

Example 9

Induction of FVIII Antigen-specific CD4+CD25+ Regulatory Cells by Fibro/F8IZ Apoptotic Cells It was next examined whether infusion of apoptotic Fibro/F8IZ cells induced the activity of antigen specific CD4+ CD25+ regulatory cells ($T_{reg}$). At 72-96 hours after the second of 2 weekly infusions of apoptotic fibroblasts, splenic CD4+ CD25+ cells were purified from treated and control mice; more than 90% of these cells expressed FOXP3 (data not shown). These CD4+CD25+ cells were cocultured with CD4+ CD25- effector T cells ($T_{eff}$) that were harvested from mice immunized with 4 doses of rhFVIII or OVA. As shown in FIG. 8C, CD4+ CD25+ cells from Fibro/F8IZ treated mice suppressed proliferation of rhFVIII stimulated effector T cells by 37.2±12.2% at a 1:5 $T_{reg}$ to $T_{eff}$ ratio and by 59.1±9.0% at a 4:5 $T_{reg}$ to $T_{eff}$ ratio. In contrast, at a 4:5 $T_{reg}$ to $T_{eff}$ ratio the CD4+ CD25+ cells from Fibro/IZ treated mice suppressed proliferation of rhFVIII stimulated effector T cells by only 9.2±7.7% and in the no cell treatment control group the suppression at this ratio was only 7.8±4.5%. For the lower ratios tested no suppression was seen with Tregs from either Fibro/IZ or no cell treatment control mice. The $T_{reg}$ from all 3 treatment groups showed an equivalent degree of suppression of OVA stimulated effector T cells from OVA immunized mice (FIG. 8C). These data show the induction of a population of antigen specific CD4+ CD25+ regulatory T cells by delivery of apoptotic fibroblasts expressing FVIII.

Example 10

Figure 8:
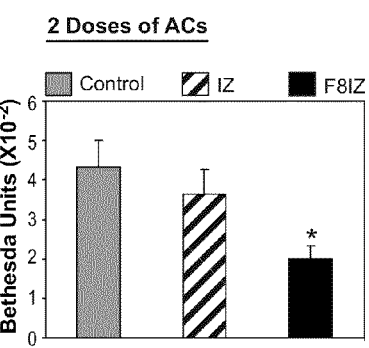
FIG. 8A is a graph showing immune suppression induced by FVIII expressing apoptotic cells after 2 weekly infusions of apoptotic fibroblasts in mice.
FIG. 8B is a set of graphs showing immune suppression and splenic T cell response induced by FVIII expressing apoptotic cells after 4 weekly infusions of apoptotic fibroblasts in mice.
FIG. 8C is a set of graphs of T cell suppression assays.
Figure 8:
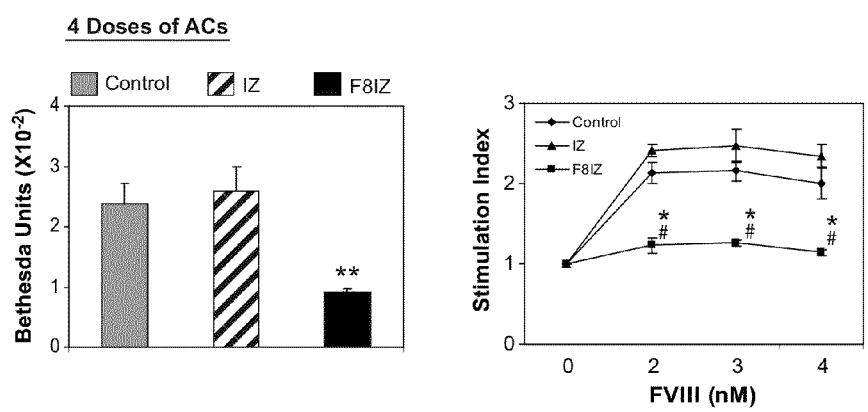
Figure 8:
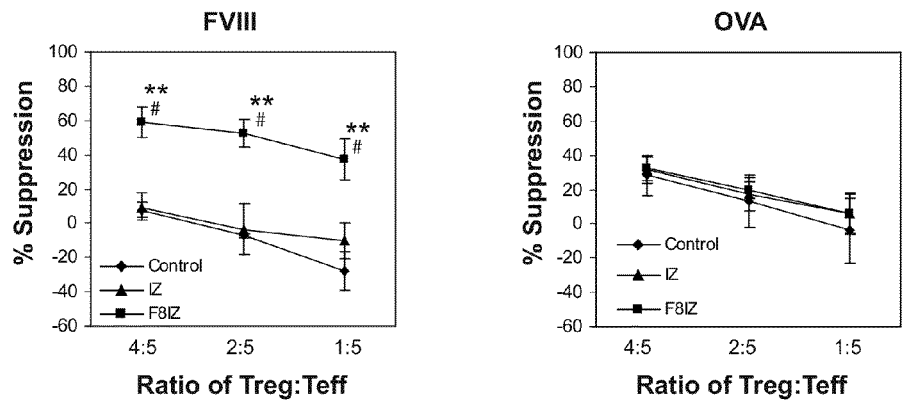

Suppression of Immune Response to FVIII is Correlated with Dose and/or Frequency of Administration of Apoptotic Cells The level of suppression of the immune response to FVIII correlated with the number of infusions of Fibro/F8IZ cells (FIGS. 5, 6, and 8). In contrast, no additional benefit was derived by giving more than $2\times10^5$ cells per infusion (FIG. 3A). Furthermore, apoptotic fibroblasts modified by a bioengineered hFVIII construct that produced 3-7 fold higher levels of hFVIII gave comparable results to fibroblasts expressing wildtype hFVIII (FIG. 10).

Figure 10:
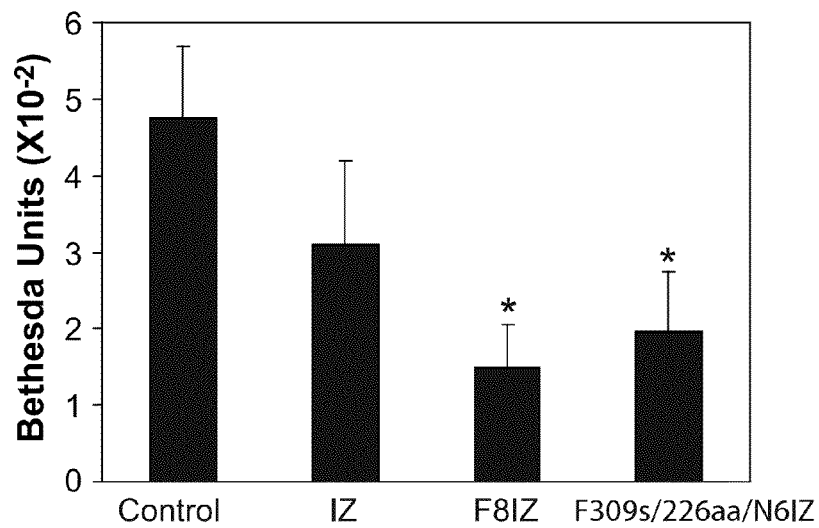
FIG. 10 is a graph showing Bethesda titers in mice treated with two weekly infusions of 1×10$^7$ UV irradiated fibroblasts expressing a full-length hFVIII transgene (Fibro/F8IZ), a bioengineered transgene lacking most of the B domain (Fibro/F309s/226aa/N61Z), or an empty vector (Fibro/IZ) prior to being challenge with four weekly doses of rhFVIII.

Hemophilic mice infused with apoptotic fibroblasts expressing a full-length or engineered FVIII transgene showed a similar degree of suppression of the immune response to FVIII (FIG. 10). Mice were treated with two weekly infusions of $1\times10^7$ UV irradiated fibroblasts expressing a full-length hFVIII transgene (Fibro/F8IZ), a bioengineered transgene lacking most of the B domain (Fibro/F309s/226aa/N61Z), or an empty vector (Fibro/IZ) prior to being challenge with four weekly doses of rhFVIII. The Fibro/F309s/226aa/N61Z cells produce 3-7 fold higher levels of FVIII than the Fibro/F8IZ cells. The Bethesda titers in both groups of mice receiving FVIII vector modified fibroblasts were significantly lower than control mice; *p<0.05 compared to no cell treatment controls, N=4-5 mice per group.

Thus, the absolute amount of FVIII antigen delivered in the apoptotic fibroblasts seems to be less important than the number of separate exposures. Without being limited to a particular theory, it is believed that Tregs may require multiple encounters with antigen to become maximally activated and/or undergo significant proliferation. In addition, the amount of cellular antigen that can be processed by tolerogenic DCs may reach a saturation point even at low and/or moderate doses of ACs.

Example 11

Isolating Human Fibroblasts

Human fibroblasts can be obtained from a variety of tissues, including biopsy specimens derived from liver, kidney, lung and skin. The procedures presented here are optimized for the isolation of skin fibroblasts, which are readily obtained from individuals of any age with minimal discomfort and risk (embryonic and fetal fibroblasts may also be isolated using the protocol). In addition, fibroblasts can be isolated from other tissues with only minor modifications to the protocol.

Human skin can be obtained following circumcision or punch biopsy. The specimen consists of three major components: the epidermal and dermal layers of the skin itself, and a fascial layer that adheres to the dermal layer. Fibroblasts can be isolated from either the dermal or facial layers.

For the isolation of Human Fascial Fibroblasts, approximately 3 cm² of tissue can be placed into approximately 10 ml of wash solution (Hank's Balanced Salt Solution containing 100 units/ml penicillin G, 100 µg/ml streptomycin sulfate, and 0.5 µg/ml Fungisone) and subjected to gentle agitation for a total of three 10-minute washes at room temperature. The tissue can then be transferred to a 100 mm tissue culture dish containing 10 ml digestion solution (wash solution containing 0.1 units/ml collagenase A, 2.4 units/ml grade II Dispase). Under a dissecting microscope, the skin can be adjusted such that the epidermis is facing down. The facial tissue is separated from the dermal and epidermal tissue by blunt dissection. The facial tissue is then cut into small fragments (less than 1 mm$^2$) and incubated on a rotating platform for 30 min at 37° C. The enzyme/cell suspension is removed and saved, an additional 10 cc of digestion solution will be added to the remaining fragments of tissue, and the tissue is reincubated for 30 min at 37° C. The enzyme/cell suspensions is pooled, passed through a 15-gauge needle several times, and passed through a Cellector Sieve (Sigma) fitted with a 150-mesh screen. The cell suspension is then centrifuged at 1100 rpm for 15 min at room temperature. The supernatant is then aspirated and the disaggregated cells are resuspended in 10 ml of nutrient medium. Fibroblast cultures are initiated on tissue culture treated flasks (Corning) at a density of approximately 40,000 cells/cm$^2$.

For the isolation of Human Dermal Fibroblasts, fascia will be removed from skin biopsy or circumcision specimen as described above and the skin is cut into small fragments less than 0.5 cm$^2$. The tissue is incubated with 0.25% trypsin for 60 min. at 37° C. Alternatively, the tissue can be incubated in trypsin for 18 hrs at 4° C. The dermis and epidermis are separated under a dissecting microscope, and dermal fibroblasts are isolated as described above for facial fibroblasts.

Example 12

Culturing Human Fibroblasts

When confluent, the primary culture is trypsinized using standard methods and seeded at approximately 10,000 cells/cm$^2$. The cells are cultured at 37° C. in humidified air containing 5% $CO_2$. Human fibroblast nutrient medium (containing DMEM, high glucose with sodium pyruvate, 10-15% calf serum, 20 mM HEPES, 20 mM L-glutamine, 50 units/ml penicillin G, and 10 µg/ml streptomycin sulfate) are changed twice weekly.

Example 13

Mode of Cell Death Dictates the Nature of the Immune Response to FVIIII

Figure 12:
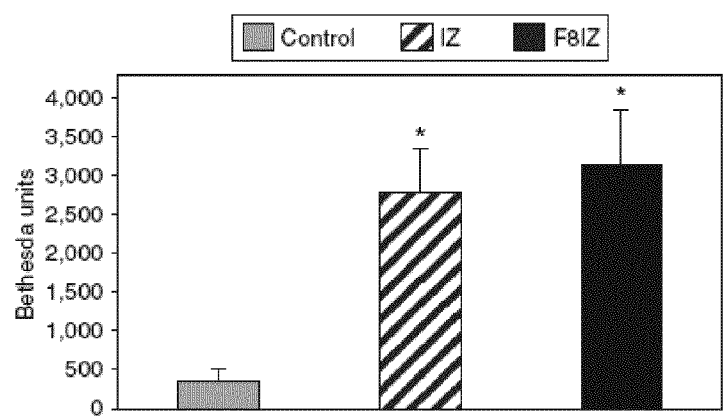
FIG. 12 is a graph showing Bethesda titers in naive hemophilic mice treated with two weekly infusions of $1 \times 10^7$ osmotically shocked Fibro/IZ cells or Fibro/F8IZ cells before being challenged with four weekly doses of rhFVIII. The data shows that Bethesda titers in both groups of fibroblast treated mice were significantly higher than the control mice that were not infused with cells prior to immunization.

A converse influence on the immune response to FVIII was observed after infusion of fibroblasts treated with osmotic shock. Mice that were immunized with rhFVIII after being infused with either osmotically shocked Fibro/F8IZ or Fibro/IZ cells developed higher Bethesda titers than mice that received no cells prior to immunization (FIG. 12). Mice were treated with two weekly infusions of 1×10$^7$ osmotically shocked Fibro/F8IZ or Fibro/IZ cells before being challenged with four weekly doses of rhFVIII. Data show that Bethesda titers in both groups of fibroblast treated mice were 7-9 fold higher than the control mice that were not infused with cells prior to immunization (* p<0.05 for cell treated vs. no cell control, N=8 for control, N=3 for Fibro/F8IZ and Fibro/IZ). Thus, dead or dying syngeneic fibroblasts modulate the immune system's response to antigen introduced along with, or shortly after, their infusion. Furthermore, the nature of the influence on the immune response depends on the mode of death of the infused cells: necrotic cells exert an immune priming effect while ACs promote the formation of tolerance.

Example 14

Hemophilic Mice Infused with Apoptotic Fibroblasts Expressing a Full-length or Engineered FVIII Transgene Show a Similar Degree of Suppression of the Immune Response to FVIII Mice were treated with two weekly infusions of 1×10$^7$ UV irradiated fibroblasts expressing a full-length hFVIII transgene (Fibro/F8IZ), a bioengineered transgene lacking most of the B domain (Fibro/F309s/226aa/N61Z), or an empty vector (Fibro/IZ) prior to challenge with four weekly doses of 0.2 µg of rhFVIII (FIG. 10). Bethesda titers were determined one week after the last dose of rhFVIII. Both groups of mice that received FVIII vector modified fibroblasts (Fibro/F8IZ and Fibro/F309s/226aa/N61Z cells) developed significantly lower Bethesda titers than control mice given no apoptotic cells prior to immune challenge (*P<0.05, N=4-5 mice per group). There was no statistical difference between suppression from the Fibro/F8IZ or Fibro/F309s/226aa/N6IZ cells.

Example 15

Dose Response to Immunization with OVA Antigen in Hemophilic Mice

Hemophilia A mice were given 4 weekly challenges with intravenous infusion of OVA, dosed at 0.2 µg, 3.3 µg, or 50 µg per infusion. One week after the last dose of OVA, mice were killed and plasma anti-OVA Ab titers were determined (FIG. 11A). Splenocytes were also harvested and in vitro T cell proliferation in response to escalating levels of OVA antigen stimulation was measured (FIG. 11B). As shown in FIGS. 11A and 11B, challenge with 4 weekly infusions of 50 µg OVA produced significantly higher anti-OVA antibody titers and T cell responses than either of the lower doses tested. Moreover, the magnitude of the anti-OVA response in mice given the 50 µg dose was similar to the anti-hFVIII response of mice that were challenged with 4 doses of 0.2 µg of rhFVIII (see FIG. 5). Thus comparing the suppression that FVIII expressing apoptotic cells have on the immune response to 4 doses of 0.2 µg of rhFVIII or 4 doses of 50 µg OVA allows determination of the antigen specificity of the immune modulation.

What is claimed:

1. A method of suppressing an immune response to Factor VIII (FVIII), comprising:
    administering apoptotic dermal fibroblast cells comprising a recombinant vector encoding FVIII antigen to a subject suffering from hemophilia A with inhibitors to FVIII, wherein the cells are syngeneic or allogeneic with the subject and effective to induce immunological tolerance in the subject to FVIII.

2. A method of suppressing an immune response to Factor VIII (FVIII), comprising:
    introducing a recombinant vector encoding FVIII antigen into dermal fibroblast cells, the cells being syngeneic or allogeneic with a subject suffering from hemophilia A with inhibitors to FVIII,
    inducing apoptosis in the cells, and
    administering the apoptotic cells to a subject suffering from hemophilia A with inhibitors to FVIII in an amount effective to induce immunological tolerance to FVIII.

3. A method of treating hemophilia A, comprising:

administering apoptotic dermal fibroblast cells comprising a recombinant vector encoding FVIII antigen to a subject suffering from hemophilia A with inhibitors to FVIII, the cells being syngeneic or allogeneic with the subject and effective to induce immunological tolerance in the subject to FVIII, and administering a therapeutically effective amount of a biologically active FVIII polypeptide to the subject.

4. The method of claim 3, wherein the biologically active FVIII polypeptide is administered as a standard course of immune tolerance induction (ITI).

5. The method of claim 4, wherein the biologically active FVIII polypeptide is administered at least 3 times per week.

6. The method of claim 1, wherein administering the apoptotic cells to the subject comprises separately administering two or more doses of the apoptotic cells, each dose being administered on a different day.

7. The method of claim 1, wherein administering the apoptotic cells to the subject comprises separately administering four or more doses of the apoptotic cells, each dose being administered on a different day.

8. The method of claim 1, wherein the subject has endogenous FVIII activity of 2% or less than normal.

9. The method of claim 1, wherein the subject has high responding inhibitors to FVIII.

10. The method of claim 9, wherein the subject is resistant to induction of immunological tolerance by administering an FVIII polypeptide in a substantially purified form.

11. The method of claim 1, wherein the immunological tolerance to FVIII is associated with a Bethesda titer of less than 5.

12. The method of claim 11, wherein the immunological tolerance to FVIII is associated with a Bethesda titer of 3 or less.

13. The method of claim 11, wherein the immunological tolerance to FVIII is associated with a Bethesda titer of 1 or less.

14. The method of claim 1, wherein the immunological tolerance to FVIII is associated with a decrease of at least 50% in Bethesda titer.

15. The method of claim 1, wherein the immunological tolerance to FVIII is associated with a decrease of at least 65% in Bethesda titer.

16. The method of claim 1, wherein the immunological tolerance to FVIII is associated with a decrease of at least 80% in Bethesda titer.

17. The method of claim 1, wherein the immunological tolerance to FVIII is transferable to naive subjects.

18. The method of claim 1, wherein the apoptotic cells are autologous with the subject.

19. The method of claim 1, wherein the recombinant vector encodes at least one immunodominant epitope of the FVIII polypeptide.

20. The method of claim 1, wherein the recombinant vector further encodes one or more additional proteins.

21. The method of claim 20, wherein the one or more additional proteins comprises an anti-inflammatory cytokine selected from interleukin-10 (IL-10) and transforming growth factor-β(TGF-β).

22. The method of claim 1, wherein the apoptotic cells have been exposed to an apoptosis-inducing amount of UV irradiation.

23. The method of claim 22, wherein the apoptosis-inducing amount of UV irradiation is effective to induce apoptosis in at least 75% of cells.

24. The method of claim 22, wherein the apoptosis-inducing amount of UV irradiation is effective to induce apoptosis in at least 75% of cells with necrosis in less than 5% of cells.

25. The method of claim 1, further comprising administering an antagonist to the CD40-CD40 ligand interaction antagonist.

26. The method of claim 25, wherein the CD40 antagonist is a blocking monoclonal anti-CD40 antibody or an anti-CD40 ligand antibody.

* * * * *